United States Patent [19]

Frommer et al.

[11] Patent Number: 5,608,146
[45] Date of Patent: Mar. 4, 1997

[54] DNA SEQUENCES WITH OLIGOSACCHARIDE TRANSPORTER, PLASMIDS, BACTERIA AND PLANTS CONTAINING A TRANSPORTER AS WELL AS A PROCESS FOR THE PREPARATION AND TRANSFORMATION OF YEAST STRAINS FOR IDENTIFICATION OF THE TRANSPORTER

[75] Inventors: Wolf-Bernd Frommer; Jorg Riesmeier, both of Berlin, Germany

[73] Assignee: Institut Für Genbiologische Forschung Berlin GmbH, Germany

[21] Appl. No.: 356,340

[22] PCT Filed: Jun. 22, 1993

[86] PCT No.: PCT/EP93/01604

§ 371 Date: Dec. 21, 1994

§ 102(e) Date: Dec. 21, 1994

[87] PCT Pub. No.: WO94/00574

PCT Pub. Date: Jan. 6, 1994

[30] Foreign Application Priority Data

Jun. 24, 1992 [DE] Germany .......................... 42 20 759.2

[51] Int. Cl.$^6$ .............................. A01H 5/00; C12N 5/10; C12N 5/04; C12N 15/29; C12N 15/82
[52] U.S. Cl. ........................ 800/205; 536/23.2; 536/23.6; 435/69.1; 435/70.1; 435/172.3; 435/320.1; 435/414; 435/417; 435/419
[58] Field of Search ................................ 435/69.1, 70.1, 435/172.3, 240.4, 320.1; 800/205; 536/23.2, 23.6

[56] References Cited

PUBLICATIONS

Napoli et al. 1990. Plant Cell 2:279–289.
Grimes et al. 1992. Plant Cell 4(12):1561–1574.
Plant Physiology, vol. 89, No. 4, Apr. 1989, Rockville, MD, U.S.A., p. 155, Ripp, K. G., et al. "cDNA Cloning and the Deduced Amino Acid Sequence of a Plasma Membrane Protein Implicated in Sucrose Transport". Supplement 4.
Plant Physiology, vol. 99, No. 1, May 1992, Rockville, MD, U.S.A., p. 84, Suppl. Overvoorde, P. J., et al. "Biochemical and Molecular Characterization of the Soybean Membrane 62kD Sucrose Binding Protein and Its Possible Role in Sucrose Transport".
Biochem. Biophys. ACTA, vol. 1103, No. 2, 1992, pp. 259–267, Li, Z–S et al., "The Sucrose Carrier of the Plant Plasmalemma: III. Partial Purification and Reconstitution of Active Sucrose Transport in Liposomes".

EMBO Journal, vol. 9, No. 10, Oct. 1990 EYNSHAM, Oxford GB, pp. 3045–3050, Sauer, N. et al., "Primary Structure, Genomic Organization and Heterologous Expression of a Glucose Transporter from Arabidopsis Thaliana".

The Plant Cell, vol. 5, No. 8 Aug. 1993, pp. 823–830, Raikhel, N. V. et al., "The Wide World of Plant Molecular Genetics" p. 825, col. 2 & NATO Advanced Study Institute Course, May 10–19, 1993.

Plant Physiology, vol. 99, No. 1 May 1992, Rockville, MD, U.S.A., p. 9, Kossman, J. et al., "Functional Analysis of the Plastidic Fructose–1,6–biphosphatase and the Triose Phosphate translocator from potato". Suppl. 1.

EMBO Journal, vol. 9, No. 10, 1990, EYNSHAM, Oxford GB pp. 3033–3044, Von Schaewen, A., et al. "Expression of a Yeast–Derived Invertase in the Cell Wall of Tabacco and Arabidopsis Plants Leads to Accumulation of Carbohydrate and Inhibition of Photosynthesis and Strongly Influences Growth and Phenotype of Transgenic Tobacco Plants".

Plant Physiology, vol. 95, 1991, Rockville, MD, U.S.A., pp. 420–425, Dickinson, C. D. et al., "Slow–Growth Phenotype of Transgenic Tomato Expressing Apoplastic Invertase".

Gene, vol. 95, 1990, Amsterdam NL, pp. 17–23, Blatch, G. L. et al., "Nucleotide Sequence and Analysis of the Vibrio Alginolyticus Sucrose Uptake–Encoding Region".

Recent Advances in Phloem Transport and Assimilate Compartmentation, Fourth International Conference, Aug. 19–24, 1990, 1991, pp. 154–166, Delrot, S., et al., "Use of Plasma Membrane Vesicles From Sugar Beet Leaves for the Study of Sucrose Transport and of Sucrose Transporters".

EMBO Journal, vol. 11, No. 13, Dec. 1992, Eynsham, Oxford GB, pp. 4705–4713, Riesmeier, J. W. et al. "Isolation and Characterization of a Sucrose Carrier cDNA from Spinach by Functional Expression in Yeast".

*Primary Examiner*—David T. Fox
*Attorney, Agent, or Firm*—Ostrolenk, Faber, Gerb & Soffen, LLP

[57] ABSTRACT

There are described DNA sequences, that contain the coding region of an oligosaccharide transporter, whose introduction in a plant genome modifies the formation and transfer of storage materials in transgenic plants, plasmids, bacteria and plants containing these DNA sequences, a process for the preparation and transformation of yeast strains, that makes possible the identification of the DNA sequences of the plant oligosaccharide transporter of the invention, as well as the use of DNA sequences of the invention.

16 Claims, 6 Drawing Sheets

DNA SEQUENCES WITH OLIGOSACCHARIDE TRANSPORTER, PLASMIDS, BACTERIA AND PLANTS CONTAINING A TRANSPORTER AS WELL AS A PROCESS FOR THE PREPARATION AND TRANSFORMATION OF YEAST STRAINS FOR IDENTIFICATION OF THE TRANSPORTER

FIELD OF THE INVENTION

The present invention relates to DNA sequences, that contain the coding region of an oligosaccharide transporter, whose introduction in a plant genome modifies the formation and transfer of storage materials in transgenic plants, plasmids, bacteria and plants containing these DNA sequences, a process for the preparation and transformation of yeast strains, that makes possible the identification of the DNA sequences of the plant oligosaccharide transporter of the invention, as well as the use of DNA sequences of the invention.

BACKGROUND OF THE INVENTION

The most important transport metabolite for stored energy in many plants, for example potatoes, is sucrose. In other species, other oligosaccharides can serve this role. In Japanese artichokes for example it is stachyose.

The central position of the oligosaccharide transport in the energy content of the plant has already been shown in transgenic plants, in which by expression of an invertase, the sucrose is split into the monosaccharides, leading to considerable changes in its habit (EP 442 592). Because of the significance of sucrose in the formation of storage materials, numerous experiments have been carried out into investigating the biosynthesis or the metabolism of disaccharides. From DE 42 13 444, it is known that the improvement of the storage properties of the harvested parts can be achieved in transgenic potatoes, in which through expression of an apoplastic invertase, the transfer of energy rich compounds to the heterotrophic parts of growing shoots is inhibited.

In spite of much effort, the mechanism for distributing storage materials, such as oligosaccharides in plants has not been clarified and, in order to influence it, it is not yet known, how the sucrose formed in the leaves following photosynthesis, reaches the transport channels of the phloem of the plant and how it is taken up from the storage organs, e.g. the tubers of potato plants or seeds. On isolated plasma membranes of cells of leaf tissue of sugar beet (*Beta vulgaris*) it has been demonstrated that the transport of sucrose through the membrane can be induced by providing an artificial pH gradient and can be intensified by providing an electrochemical potential (Lemoine & Delrot (1989) FEBS letters 249: 129–133). The membrane passage of sucrose follows a Michaelis-Menten kinetic, in which the $k_m$ value of the sucrose transport is around 1 mM (Slone & Buckbout, 1991, Planta 183: 484–589). This form of kinetic indicates the involvement of transporter protein. Experiments on plasma membranes of sugar beet, *Ricinus communis* and *Cyclamen persicum* has shown that the sucrose transport is concerned with a cotransport of protons (Buckhout, 1989, Planta 178: 393–399; Williams et al., 1990, Planta 182: 540–545; Grimm et al., 1990, Planta 182: 480–485). The stoichiometry of the cotransport is 1:1 (Bush, 1990, Plant Physiol 93: 1590–1596). Mechanisms have also been proposed however, for transport of the sucrose through the plasmodium of the plant cells (Robards & Lucas, 1990, Ann Rev Plant Physiol 41: 369–419). In spite of the knowledge of the existence of an active transport system, that allows the cells to deliver sucrose to the transport channels, a protein with these kind of properties is not yet known. In N-ethylmaleinimide staining of sugar beet plasma membrane in the presence and absence of sucrose Gallet et al. (1989, Biochem Biophys Acta 978: 56–64) obtained information that a protein of size 42 kDa can interact with sucrose. Antibodies against a fraction of plasma membrane protein of this size range can inhibit the sucrose transport through plasma membranes (Lemoine et al., 1989, Bichem Biophys Acta 978: 65–71). In contrast, information has been obtained (Ripp et al., 1988, Plant Physiol 88: 1435–1445) by the photoaffinity marking of soyabean protein with the sucrose analogue, desoxyazidohydroxybenzamidosucrose, on the participation of a 62 kDa protein in the transport of sucrose through membranes. An amino acid sequence of a sucrose transporter is not known.

SUMMARY OF THE INVENTION

There are now described DNA sequences which contain the coding region of an oligosaccharide transporter, and whose information contained in the nucleotide sequence allows, by sequence integration in a plant genome, the formation of RNA, by which a new oligosaccharide transport activity can be introduced in the plant cells or an endogenous oligosaccharide transporter activity can be expressed. By the term oligosaccharides transporter is for example to the understood a sucrose transporter from plants such as spinach or potatoes.

The identification of the coding region of the oligosaccharide transporter is carried out by a process which allows the isolation of plant DNA sequences which code the transporter molecules by means of expression in specific mutants of yeast *Saccharomyces cerevisiae*. For this, suitable yeast mutants have to be provided which cannot take up a substance for which the coding region of a transporter molecule has to be isolated from a plant gene library. A process is already known for complementation of a potassium transport deficiency in yeast mutants (Anderson et al., 1992, Proc Natl Acad Sci USA 89: 3736–3740). In this, yeast cDNA sequences for plant mRNA are expressed in yeast mutants by use of expression vectors. Those yeasts which can now take up the substances to be transported into the cells, contain the coding region for a transporter molecule in the expression vector. The known process is however not useful for identification of the coding region for a sucrose transporter, since yeasts contain no endogenous sucrose transporter which could be switched off through mutation. Yeasts code a cleaving invertase, which cleaves extracellular sucrose so that hexoses can be taken up from the cells via a hexose transporter.

DETAILED DESCRIPTION OF THE INVENTION

Figure 1:
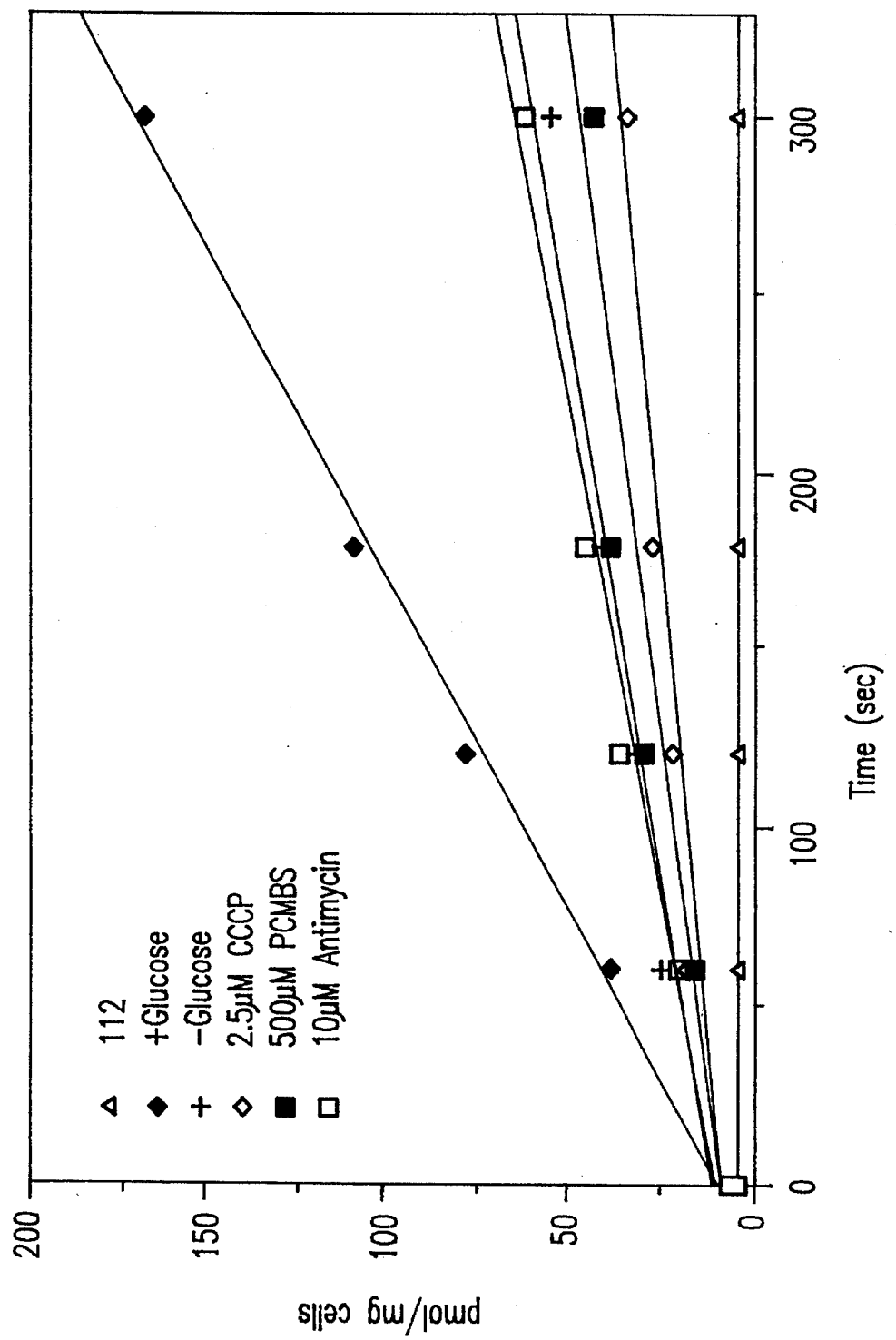
FIG. 1 is a graph of the uptake of sucrose in yeast cells over time.

For the preparation and transformation of yeast strains which serve to identify a plant oligosaccharide transporter:
a) first, a yeast strain with a defective suc2 gene, which cannot be cleaved by invertase, is prepared by homologous recombination and then from this,
b) by transformation with a gene for a sucrose synthase activity from plant cells, a yeast strain which can cleave intracellular sucrose is extracted, and
c) by transformation of this strain with a plant cDNA library in an expression vector for yeast cells, the DNA sequence, which codes for a plant oligosaccharide transporter, is identified.

The yeast strains obtained from this process, for identification of plant oligosaccharide transporters are for example the yeast strains YSH 2.64-1A-SUSY (DSM 7106) and YSH 2.64-1A-INV (DSM 7105).

With the yeast strain YSH 2.64-1A-SUSY, a DNA sequence for a plant sucrose transporter is identified which has the following sequences.

Sucrose-Transporter from spinach (Seq. ID No.1 and No.2):

```
AAAAACACAC ACCCAAAAAA AAAACACTAC GACTATTTCA AAAAAAACAT TGTTACTAGA        60

AATCTTATT  ATG GCA GGA AGA AAT ATA AAA AAT GGT GAA AAT AAC              105
           Met Ala Gly Arg Asn Ile Lys Asn Gly Glu Asn Asn
           1               5                   10

AAG ATT GCG GGT TCT TCT CTT CAC TTA GAG AAG AAC CCA ACA ACT             150
Lys Ile Ala Gly Ser Ser Leu His Leu Glu Lys Asn Pro Thr Thr
        15              20              25

CCC CCC GAG GCC GAG GCT ACC TTA AAG AAG CTC GGC CTC GTG GCT             195
Pro Pro Glu Ala Glu Ala Thr Leu Lys Lys Leu Gly Leu Val Ala
        30              35              40

TCA GTA GCG GCC GGG GTT CAG TTC GGG TGG GCT TTA CAG CTC TCC             240
Ser Val Ala Ala Gly Val Gln Phe Gly Trp Ala Leu Gln Leu Ser
        45              50              55

CTA CTG ACC CCG TAC GTC CAA CTA CTG GGC ATT CCC CAC ACT TGG             285
Leu Leu Thr Pro Tyr Val Gln Leu Leu Gly Ile Pro His Thr Trp
        60              65              70

GCC GCC TAC ATC TGG TTG TGC GGC CCA ATC TCG GGG ATG ATT GTC             330
Ala Ala Tyr Ile Trp Leu Cys Gly Pro Ile Ser Gly Met Ile Val
        75              80              85

CAG CCA TTG GTC GGG TAC TAT AGT GAC CGG TGC ACC TCC CGC TTC             375
Gln Pro Leu Val Gly Tyr Tyr Ser Asp Arg Cys Thr Ser Arg Phe
        90              95              100

GGC CGA CGT CGC CCC TTC ATT GCA GCA GGG GCG GCT CTA GTG GCC             420
Gly Arg Arg Arg Pro Phe Ile Ala Ala Gly Ala Ala Leu Val Ala
        105             110             115

GTA GCG GTG GGG CTA ATC GGA TTC GCC GCC GAT ATC GGC GCA GCG             465
Val Ala Val Gly Leu Ile Gly Phe Ala Ala Asp Ile Gly Ala Ala
        120             125             130

TCG GGT GAT CCA ACG GGA AAC GTG GCA AAA CCC CGG GCC ATC GCG             510
Ser Gly Asp Pro Thr Gly Asn Val Ala Lys Pro Arg Ala Ile Ala
        135             140             145

GTG TTT GTG GTC GGG TTT TGG ATC CTC GAC GTG GCT AAC AAC ACC             555
Val Phe Val Val Gly Phe Trp Ile Leu Asp Val Ala Asn Asn Thr
        150             155             160

CTG CAA GGC CCA TGC AGG GCG TTG TTA GCA GAC ATG GCC GCC GGG             600
Leu Gln Gly Pro Cys Arg Ala Leu Leu Ala Asp Met Ala Ala Gly
        165             170             175

TCG CAA ACC AAA ACC CGG TAC GCT AAC GCC TTC TTC TCC TTC TTC             645
Ser Gln Thr Lys Thr Arg Tyr Ala Asn Ala Phe Phe Ser Phe Phe
        180             185             190

ATG GCG TTA GGA AAC ATC GGA GGG TAC GCC GCC GGT TCA TAC AGC             690
Met Ala Leu Gly Asn Ile Gly Gly Tyr Ala Ala Gly Ser Tyr Ser
        195             200             205

CGC CTC TAC ACG GTG TTC CCC TTT ACC AAA ACC GCC GCC TGC GAC             735
Arg Leu Tyr Thr Val Phe Pro Phe Thr Lys Thr Ala Ala Cys Asp
        210             215             220

GTC TAC TGC GCC AAT CTA AAA TCC TGC TTC TTC ATC TCC ATC ACA             780
Val Tyr Cys Ala Asn Leu Lys Ser Cys Phe Phe Ile Ser Ile Thr
        225             230             235
```

| | | | | | | | | | | | | | | |
|---|---|---|---|---|---|---|---|---|---|---|---|---|---|---|
| CTC | CTA | ATC | GTC | CTC | ACA | ATC | CTA | GCA | CTT | TCC | GTC | GTA | AAA | GAG |
| Leu | Leu | Ile 240 | Val | Leu | Thr | Ile 245 | Leu | Ala | Leu | Ser | Val | Val 250 | Lys | Glu |

825

| | | | | | | | | | | | | | | |
|---|---|---|---|---|---|---|---|---|---|---|---|---|---|---|
| CGT | CAA | ATC | ACA | ATC | GAC | GAA | ATC | CAA | GAA | GAA | GAA | GAC | TTA | AAA |
| Arg | Gln | Ile 255 | Thr | Ile | Asp | Glu 260 | Ile | Gln | Glu | Glu | Glu 265 | Asp | Leu | Lys |

870

| | | | | | | | | | | | | | | |
|---|---|---|---|---|---|---|---|---|---|---|---|---|---|---|
| AAC | AGA | AAC | AAT | AGC | AGC | GGT | TGT | GCA | AGA | CTA | CCG | TTC | TTC | GGA |
| Asn | Arg | Asn 270 | Asn | Ser | Ser | Gly 275 | Cys | Ala | Arg | Leu | Pro 280 | Phe | Phe | Gly |

915

| | | | | | | | | | | | | | | |
|---|---|---|---|---|---|---|---|---|---|---|---|---|---|---|
| CAA | TTA | ATA | GGC | GCT | CTC | AAA | GAT | CTA | CCA | AAA | CCA | ATG | CTA | ATC |
| Gln | Leu | Ile 285 | Gly | Ala | Leu | Lys 290 | Asp | Leu | Pro | Lys | Pro 295 | Met | Leu | Ile |

960

| | | | | | | | | | | | | | | |
|---|---|---|---|---|---|---|---|---|---|---|---|---|---|---|
| CTA | TTA | CTA | GTA | ACA | GCC | CTA | AAT | TGG | ATC | GCA | TGG | TTT | CCA | TTC |
| Leu | Leu | Leu 300 | Val | Thr | Ala | Leu 305 | Asn | Trp | Ile | Ala | Trp 310 | Phe | Pro | Phe |

1005

| | | | | | | | | | | | | | | |
|---|---|---|---|---|---|---|---|---|---|---|---|---|---|---|
| TTG | TTG | TTC | GAT | ACT | GAT | TGG | ATG | GGT | AAA | GAA | GTG | TAC | GGT | GGT |
| Leu | Leu | Phe 315 | Asp | Thr | Asp | Trp 320 | Met | Gly | Lys | Glu | Val 325 | Tyr | Gly | Gly |

1050

| | | | | | | | | | | | | | | |
|---|---|---|---|---|---|---|---|---|---|---|---|---|---|---|
| ACA | GTC | GGA | GAA | GGT | AAA | TTG | TAC | GAC | CAA | GGA | GTT | CAT | GCC | GGT |
| Thr | Val | Gly 330 | Glu | Gly | Lys | Leu 335 | Tyr | Asp | Gln | Gly | Val 340 | His | Ala | Gly |

1095

| | | | | | | | | | | | | | | |
|---|---|---|---|---|---|---|---|---|---|---|---|---|---|---|
| GCC | TTA | GGT | CTG | ATG | ATT | AAC | TCC | GTT | GTC | TTA | GGT | GTT | ATG | TCG |
| Ala | Leu | Gly 345 | Leu | Met | Ile | Asn 350 | Ser | Val | Val | Leu | Gly 355 | Val | Met | Ser |

1140

| | | | | | | | | | | | | | | |
|---|---|---|---|---|---|---|---|---|---|---|---|---|---|---|
| TTG | AGT | ATT | GAA | GGT | TTG | GCT | CGT | ATG | GTA | GGC | GGT | GCT | AAA | AGG |
| Leu | Ser | Ile 360 | Glu | Gly | Leu | Ala 365 | Arg | Met | Val | Gly | Gly 370 | Ala | Lys | Arg |

1185

| | | | | | | | | | | | | | | |
|---|---|---|---|---|---|---|---|---|---|---|---|---|---|---|
| TTA | TGG | GGA | ATT | GTC | AAT | ATT | ATT | CTT | GCT | GTT | TGT | TTA | GCT | ATG |
| Leu | Trp | Gly 375 | Ile | Val | Asn | Ile 380 | Ile | Leu | Ala | Val | Cys 385 | Leu | Ala | Met |

1230

| | | | | | | | | | | | | | | |
|---|---|---|---|---|---|---|---|---|---|---|---|---|---|---|
| ACG | GTG | TTA | GTT | ACT | AAG | TCC | GCC | GAA | CAC | TTC | CGT | GAT | AGC | CAC |
| Thr | Val | Leu 390 | Val | Thr | Lys | Ser 395 | Ala | Glu | His | Phe | Arg 400 | Asp | Ser | His |

1275

| | | | | | | | | | | | | | | |
|---|---|---|---|---|---|---|---|---|---|---|---|---|---|---|
| CAT | ATT | ATG | GGC | TCC | GCC | GTC | CCT | CCG | CCG | CCG | CCT | GCT | GGT | GTT |
| His | Ile | Met 405 | Gly | Ser | Ala | Val 410 | Pro | Pro | Pro | Pro | Pro 415 | Ala | Gly | Val |

1320

| | | | | | | | | | | | | | | |
|---|---|---|---|---|---|---|---|---|---|---|---|---|---|---|
| AAG | GGT | GGC | GCT | TTG | GCT | ATC | TTT | GCC | GTT | CTT | GGT | ATC | CCT | CTT |
| Lys | Gly | Gly 420 | Ala | Leu | Ala | Ile 425 | Phe | Ala | Val | Leu | Gly 430 | Ile | Pro | Leu |

1365

| | | | | | | | | | | | | | | |
|---|---|---|---|---|---|---|---|---|---|---|---|---|---|---|
| GCG | ATC | ACT | TTC | AGT | ATT | CCT | TTG | GCC | TTG | GCG | TCA | ATC | TTT | TCA |
| Ala | Ile | Thr 435 | Phe | Ser | Ile | Pro 440 | Leu | Ala | Leu | Ala | Ser 445 | Ile | Phe | Ser |

1410

| | | | | | | | | | | | | | | |
|---|---|---|---|---|---|---|---|---|---|---|---|---|---|---|
| GCA | TCT | TCC | GGT | TCA | GGA | CAA | GGT | CTT | TCT | CTA | GGA | GTT | CTC | AAC |
| Ala | Ser | Ser 450 | Gly | Ser | Gly | Gln 455 | Gly | Leu | Ser | Leu | Gly 460 | Val | Leu | Asn |

1455

| | | | | | | | | | | | | | | |
|---|---|---|---|---|---|---|---|---|---|---|---|---|---|---|
| CTC | GCC | ATC | GTT | GTA | CCC | CAG | ATG | TTT | GTG | TCG | GTA | ACA | AGT | GGG |
| Leu | Ala | Ile 465 | Val | Val | Pro | Gln 470 | Met | Phe | Val | Ser | Val 475 | Thr | Ser | Gly |

1500

| | | | | | | | | | | | | | | |
|---|---|---|---|---|---|---|---|---|---|---|---|---|---|---|
| CCA | TGG | GAT | GCA | ATG | TTT | GGT | GGA | GGA | AAT | TTG | CCA | GCA | TTC | GTG |
| Pro | Trp | Asp 480 | Ala | Met | Phe | Gly 485 | Gly | Gly | Asn | Leu | Pro 490 | Ala | Phe | Val |

1545

| | | | | | | | | | | | | | | |
|---|---|---|---|---|---|---|---|---|---|---|---|---|---|---|
| GTG | GGA | GCT | GTA | GCA | GCA | ACA | GCC | AGT | GCA | GTT | CTT | TCA | TTT | ACA |
| Val | Gly | Ala 495 | Val | Ala | Ala | Thr 500 | Ala | Ser | Ala | Val | Leu 505 | Ser | Phe | Thr |

1590

| | | | | | | | | | | | | | | |
|---|---|---|---|---|---|---|---|---|---|---|---|---|---|---|
| TTG | TTG | CCT | TCT | CCA | CCC | CCT | GAA | GCT | AAA | ATT | GGT | GGG | TCC | ATG |
| Leu | Leu | Pro 510 | Ser | Pro | Pro | Pro 515 | Glu | Ala | Lys | Ile | Gly 520 | Gly | Ser | Met |

1635

| | | | |
|---|---|---|---|
| GGT | GGT | CAT | TAAGAAATTT AATACTACTC CGTACAATTT AAACCCAAAT |
| Gly | Gly | His 525 | |

1684

TAAAAATGAA AATGAAAATT TTTAACCCAT GTTCGTTACG TTGTAATTAG

1734

-continued

```
AGAGAAAAAT GATATATTGA ACGAAGCCGT TAATTTATGC TCCGTTCATC          1784

TTGTAATTCT TTTTCTCTCT GCTTTTTTTT TTTTTTTTTA ACGCGACGTG          1834

TTTTTGAGAT AAGGAAGGGC TAGATCGAGG ATGGGGGAAT TGGCAAGAAA          1884

TTGCTCGGGT ATAAATATTT ATCCCTCTTT GTAATTTTCA GTAACATTTA          1934

ATAGCCAGAA ATCAAAAAGT CAAGAAAAAT CGAAA                          1969
```

Sucrose Transporter from potato (Seq-ID No. 3 and No. 4):

```
                                                    AAAA                    4

ATG GAG AAT GGT ACA AAA AGA GAA GGT TTA GGG AAA CTT ACA GTT                49
Met Glu Asn Gly Thr Lys Arg Glu Gly Leu Gly Lys Leu Thr Val
              5                   10                  15

TCA TCT TCT CTA CAA GTT GAA CAG CCT TTA GCA CCA TCA AAG CTA                94
Ser Ser Ser Leu Gln Val Glu Gln Pro Leu Ala Pro Ser Lys Leu
              20                  25                  30

TGG AAA ATT ATA GTT GTA GCT TCC ATA GCT GCT GGT GTT CAA TTT                139
Trp Lys Ile Ile Val Val Ala Ser Ile Ala Ala Gly Val Gln Phe
              35                  40                  45

GGT TGG GCT CTT CAG CTC TCT TTG CTT ACA CCT TAT GTT CAA TTG                184
Gly Trp Ala Leu Gln Leu Ser Leu Leu Thr Pro Tyr Val Gln Leu
              50                  55                  60

CTC GGA ATT CCT CAT AAA TTT GCC TCT TTT ATT TGG CTT TGT GGA                229
Leu Gly Ile Pro His Lys Phe Ala Ser Phe Ile Trp Leu Cys Gly
              65                  70                  75

CCG ATT TCT GGT ATG ATT GTT CAG CCA GTT GTG GGC TAC TAC AGT                274
Pro Ile Ser Gly Met Ile Val Gln Pro Val Val Gly Tyr Tyr Ser
              80                  85                  90

GAT AAT TGC TCC TCC CGT TTC GGT CGC CGC CGG CCA TTC ATT GCC                319
Asp Asn Cys Ser Ser Arg Phe Gly Arg Arg Arg Pro Phe Ile Ala
              95                  100                 105

GCC GGA GCT GCA CTT GTT ATG ATT GCG GTT TTC CTC ATC GGA TTC                364
Ala Gly Ala Ala Leu Val Met Ile Ala Val Phe Leu Ile Gly Phe
              110                 115                 120

GCC GCC GAC CTT GGT CAC GCC TCC GGT GAC ACT CTC GGA AAA GGA                409
Ala Ala Asp Leu Gly His Ala Ser Gly Asp Thr Leu Gly Lys Gly
              125                 130                 135

TTT AAG CCA CGT GCC ATT GCC GTT TTC GTC GTC GGC TTT TGG ATC                454
Phe Lys Pro Arg Ala Ile Ala Val Phe Val Val Gly Phe Trp Ile
              140                 145                 150

CTT GAT GTT GCT AAC AAC ATG TTA CAG GGC CCA TGC AGA GCA CTA                499
Leu Asp Val Ala Asn Asn Met Leu Gln Gly Pro Cys Arg Ala Leu
              155                 160                 165

CTG GCT GAT CTC TCC GGC GGA AAA TCC GGC AGG ATG AGA ACA GCA                544
Leu Ala Asp Leu Ser Gly Gly Lys Ser Gly Arg Met Arg Thr Ala
              170                 175                 180

AAT GCT TTT TTC TCA TTC TTC ATG GCC GTC GGA AAC ATT CTG GGG                589
Asn Ala Phe Phe Ser Phe Phe Met Ala Val Gly Asn Ile Leu Gly
              185                 190                 195

TAC GCC GCC GGT TCA TAT TCT CAC CTC TTT AAA GTA TTC CCC TTC                634
Tyr Ala Ala Gly Ser Tyr Ser His Leu Phe Lys Val Phe Pro Phe
              200                 205                 210

TCA AAA ACC AAA GCC TGC GAC ATG TAC TGC GCA AAT CTG AAG AGT                679
Ser Lys Thr Lys Ala Cys Asp Met Tyr Cys Ala Asn Leu Lys Ser
              215                 220                 225

TGT TTC TTC ATC GCT ATA TTC CTT TTA CTC AGC TTA ACA ACC ATA                724
Cys Phe Phe Ile Ala Ile Phe Leu Leu Leu Ser Leu Thr Thr Ile
              230                 235                 240
```

| | | |
|---|---|---|
| GCC TTA ACC TTA GTC CGG GAA AAC GAG CTC CCG GAG AAA GAC GAG<br>Ala Leu Thr Leu Val Arg Glu Asn Glu Leu Pro Glu Lys Asp Glu<br>245 250 255 | | 769 |
| CAA GAA ATC GAC GAG AAA TTA GCC GGC GCC GGA AAA TCG AAA GTA<br>Gln Glu Ile Asp Glu Lys Leu Ala Gly Ala Gly Lys Ser Lys Val<br>260 265 270 | | 814 |
| CCG TTT TTC GGT GAA ATT TTT GGG GCT TTG AAA GAA TTA CCT CGA<br>Pro Phe Phe Gly Glu Ile Phe Gly Ala Leu Lys Glu Leu Pro Arg<br>275 280 285 | | 859 |
| CCG ATG TGG ATT CTT CTA TTA GTA ACC TGT TTG AAC TGG ATC GCG<br>Pro Met Trp Ile Leu Leu Leu Val Thr Cys Leu Asn Trp Ile Ala<br>290 300 305 | | 904 |
| TGG TTT CCC TTT TTC TTA TAC GAT ACA GAT TGG ATG GCT AAG GAG<br>Trp Phe Pro Phe Phe Leu Tyr Asp Thr Asp Trp Met Ala Lys Glu<br>310 315 320 | | 949 |
| GTT TTC GGT GGA CAA GTC GGT GAT GCG AGG TTG TAC GAT TTG GGT<br>Val Phe Gly Gly Gln Val Gly Asp Ala Arg Leu Tyr Asp Leu Gly<br>325 330 335 | | 994 |
| GTA CGC GCT GGT GCA ATG GGA TTA CTG TTG CAA TCT GTG GTT CTA<br>Val Arg Ala Gly Ala Met Gly Leu Leu Leu Gln Ser Val Val Leu<br>340 345 350 | | 1039 |
| GGG TTT ATG TCA CTT GGG GTT GAA TTC TTA GGG AAG AAG ATT GGT<br>Gly Phe Met Ser Leu Gly Val Glu Phe Leu Gly Lys Lys Ile Gly<br>355 360 370 | | 1084 |
| GGT GCT AAG AGG TTA TGG GGA ATT TTG AAC TTT GTT TTG GCT ATT<br>Gly Ala Lys Arg Leu Trp Gly Ile Leu Asn Phe Val Leu Ala Ile<br>375 380 385 | | 1129 |
| TGC TTG GCT ATG ACC ATT TTG GTC ACC AAA ATG GCC GAG AAA TCT<br>Cys Leu Ala Met Thr Ile Leu Val Thr Lys Met Ala Glu Lys Ser<br>390 395 400 | | 1174 |
| CGC CAG CAC GAC CCC GCC GGC ACA CTT ATG GGG CCG ACG CCT GGT<br>Arg Gln His Asp Pro Ala Gly Thr Leu Met Gly Pro Thr Pro Gly<br>405 410 415 | | 1219 |
| GTT AAA ATC GGT GCC TTG CTT CTC TTT GCC GCC CTT GGT ATT CCT<br>Val Lys Ile Gly Ala Leu Leu Leu Phe Ala Ala Leu Gly Ile Pro<br>420 425 430 | | 1264 |
| CTT GCG GCA ACT TTT AGT ATT CCA TTT GCT TTG GCA TCT ATA TTT<br>Leu Ala Ala Thr Phe Ser Ile Pro Phe Ala Leu Ala Ser Ile Phe<br>435 440 445 | | 1309 |
| TCT AGT AAT CGT GGT TCA GGA CAA GGT TTG TCA CTA GGA GTG CTC<br>Ser Ser Asn Arg Gly Ser Gly Gln Gly Leu Ser Leu Gly Val Leu<br>450 455 460 | | 1354 |
| AAT CTT GCA ATT GTT GTA CCA CAG ATG TTG GTG TCA CTA GTA GGA<br>Asn Leu Ala Ile Val Val Pro Gln Met Leu Val Ser Leu Val Gly<br>465 470 475 | | 1399 |
| GGG CCA TGG GAT GAT TTG TTT GGA GGA GGA AAC TTG CCT GGA TTT<br>Gly Pro Trp Asp Asp Leu Phe Gly Gly Gly Asn Leu Pro Gly Phe<br>480 485 490 | | 1444 |
| GTA GTT GGA GCA GTT GCA GCT GCC GCG AGC GCT GTT TTA GCA CTC<br>Val Val Gly Ala Val Ala Ala Ala Ala Ser Ala Val Leu Ala Leu<br>495 500 505 | | 1489 |
| ACA ATG TTG CCA TCT CCA CCT GCT GAT GCT AAG CCA GCA GTC GCC<br>Thr Met Leu Pro Ser Pro Pro Ala Asp Ala Lys Pro Ala Val Ala<br>510 515 520 | | 1534 |
| ATG GGG CTT TCC ATT AAA TAATTACAAA AGAAGGAGAA GAACAACTTT<br>Met Gly Leu Ser Ile Lys<br>525 | | 1582 |
| TTTTTAATAT TAGTACTTCT CTTTTGTAAA CTTTTTTTAT TTTAGAAAAC | | 1632 |
| AAACATAACA TGGAGGCTAT CTTTACAAGT GGCATGTCCA TGTATCTTCC | | 1682 |

-continued

TTTTTTCATA AAGCTCTTTA GTGGAAGAAG AATTAGAGGA AGTTTCCTTT  1732

TAATTTCTTC CAAACAAATG GGGTATGTGT AGTTGTTTTC A  1773

The identified DNA sequences can be introduced into plasmids and thereby be combined with steering elements for expression in eukaryotic cells (see Example 5). These steering elements are on the one hand transcription promoters, and on the other hand transcription terminators. With the DNA sequences of the invention contained on the plasmids, eukaryotic cells can be transformed, with the aim of expression of a translatable mRNA which makes possible the synthesis of a sucrose transporter in the cells or with the aim of expression of a non-translatable RNA, which prevents synthesis of an endogenous sucrose transporter in the cells. By expression of an RNA corresponding to the inventive sequences of the oligosaccharide transporter, a modification of the plant carbohydrate metabolism is possible, which can be of significance in that an improvement in the delivery of storage substances in the harvested parts results in an increase in yield of agricultural plants. The possibility of forcing the uptake of storage materials in individual organs allows the modification of the whole plant by which the growth of individual tissues, for example leaves, is slowed down, whilst the growth of the harvested parts is increased. For this, one can imagine a lengthening of the vegetative phase of crops, which leads to an increased formation of storage substances.

Processes for the genetic modification of dicotyledonous and monocotyledonous plants are already known, (see for example Gasser, C. S., Fraley, R. T., 1989, Science 244: 1293–1299; Potrykus, 1991, Ann Rev Plant Mol Biol Plant Physiol 42: 205–225). For expression in plants—the coding sequences must be coupled with the transcriptional regulatory elements. Such elements called promoters, are known (EP 375091).

Further, the coding regions must be provided with transcription termination signals with which they can be correctly transcribed. Such elements are also described (see Gielen et al., 1989, EMBO J 8: 23–29). The transcriptional start region can be native and/or homologous as well as foreign and/or heterologous to the host plant. If desired, termination regions are interchangeable with one another. The DNA sequence of the transcription starting and termination regions can be prepared synthetically or obtained naturally, or obtained from a mixture of synthetic and natural DNA constituents. For introduction of foreign genes in higher plants a large number of cloning vectors are available that include a replication signal for E. coli and a marker which allows selection of the transformed cells. Examples of such vectors are pBR 322, pUC-Series, M13 mp-Series, pACYC 184 etc. Depending on the method of introduction of the desired gene in the plants, other DNA sequences may be suitable. Should the Ti- or Ri-plasmid be used, e.g. for the transformation of the plant cell, then at least the right boundary, often however both the right and left boundary of the Ti- and Ri-Plasmid T-DNA, is attached, as a flanking region, to the gene being introduced. The use of T-DNA for the transformation of plants cells has been intensively researched and is well described in EP 120 516; Hoekama, In: The Binary Plant Vector System, Offset-drukkerij Kanters B. V. Alblasserdam, (1985), Chapter V; Fraley, et al., Crit. Rev. Plant Sci., 4:1–46 and An et al. (1985) EMBO J. 4: 277–287. Once the introduced DNA is integrated in the genome, it is generally stably incorporated and remains also in the offspring of the original transformed cells. It normally contains a selection marker, which induces resistance in the transformed plant cells against a biocide or antibiotic such as kanamycin, G 418, bleomycin, hygromycin or phosphinotricin etc. The individual marker employed should therefore allow the selection of transformed cells from cells which lack the introduced DNA.

For the introduction of DNA into a plant host cell, besides transformation using Agrobacteria, there are many other techniques available. These techniques include the fusion of protoplasts, microinjection of DNA and electroporation, as well as ballistic methods and virus infection. From the transformed plant material, whole plants can be regenerated in a suitable medium, which contains antibiotics or biocides for the selection. The resulting plants can then be tested for the presence of introduced DNA. No special demands are placed on the plasmids in injection and electroporation. Simple plasmids, such as e.g. pUC-derivatives can be used. Should however whole plants be regenerated from such transformed cells the presence of a selectable marker gene is necessary. The transformed cells grow within the plants in the usual manner (see also McCormick et al. (1986) Plant Cell Reports 5: 81–84). These plants can be grown normally and crossed with plants that possess the same transformed genes or different genes. The resulting hybrid individuals have the corresponding phenotypical properties.

The DNA sequences of the invention can also be introduced in plasmids and thereby combined with steering elements for an expression in prokaryotic cells. The formation of a translatable RNA sequence of a eukaryotic sucrose transporter from bacteria leads, in spite of the considerable differences in the membrane structures of prokaryotes and eukaryotes, to prokaryotes which are able to take up sucrose. This makes possible the production of technically interesting bacterial strains, which could be grown on the relatively cheap substrate sucrose (see Example 5). For example, the production of polyhydroxybutyric acid in the bacteria *Alkaligenes eutrophus* is described (Steinbüchel & Schubert, 1989, Arch Microbiol 153: 101–104). The bacterium only uses however a very limited selection of substrates. The expression of a gene for a sucrose transporter, amongst others, in *Alkaligenes eutrophus* would therefore be of great interest.

The DNA sequences of the invention can also be introduced in plasmids which allow mutagenesis or a sequence modification through recombination of DNA sequences in prokaryotic or eukaryotic systems. In this way the specificity of the sucrose transporter can be modified.

By using standard processes (see Sambrook et al., 1989, Molecular Cloning: A Laboratory Manual, 2. Edn., Cold Spring Harbor Laboratory Press, N.Y., USA), base exchanges can be carried out or natural or synthetic sequences can be added. For binding DNA fragments with one another adaptors or linkers can be introduced on the fragments. Further, manipulations can be carried which prepare suitable restriction cleavage sides or remove the excess DNA or restriction cleavage sites. Where insertions, deletions or substitutions such as, for example transitions and transversions, are to be carried out, in vitro mutagenesis, primer repair, restrictions or ligations can be used. For methods of analysis, in general a sequence analysis, restriction analysis and other biochemical molecular biological methods can be used. After each manipulation, the DNA sequence used can be cleaved and bound with another DNA sequence. Each plasmid sequence can be cloned in the same or different plasmids.

Derivatives or parts of the DNA sequences and plasmids of the invention can also be used for the transformation of prokaryotic and eukaryotic cells. Further, the DNA sequences of the invention can be used according to standard processes for the isolation of similar sequences on the genome of plants of various species, which also code for sucrose or other oligosaccharide transporter molecules. With these sequences, constructs for the transformation of plant cells can be prepared which modify the transport process in transgenic plants.

In order to specify related DNA sequences, gene libraries must first be prepared, which are representative of the content in genes of a plant type or of the expression of genes in a plant type. The former are genomic libraries, while the latter are cDNA libraries. From these, related sequences can be isolated using the DNA sequences of the invention as probes. Once the related gene has been identified and isolated, a determination of the sequence and an analysis of the properties of the proteins coded from this sequence is possible.

In order to understand the examples forming the basis of this invention all the processes necessary for these tests and which are known per se will first be listed:

1. Cloning process

For cloning, there was used the phage Lambda ZAP II, as well as the vector pBluescriptSK (Short et al., 1988, Nucl Acids Res 16: 7583–7600).

For the transformation of yeasts, the vectors YIplac 128 and YEplac 112 (Gietz & Sugino, 1988, Gene 74: 527–534) were used.

For the plant transformation, the gene constructs in the binary vector pBinAR (Höfgen & Willmitzer, 1990, Plant Sci 66: 221–230) were cloned.

2. Bacterial and yeast strains

For the pBbluescriptSK vector as well as for PBinAR constructs, the *E. coli* strain XLlblue (Bullock et al., 1987, Biotechniques, 5, 376–378) was used.

As starting strain for the production of yeast strain YSH 2.64-1A-susy of the invention, the strain YSH 2.64-1A (Gozalbo & Hohmann, 1990, Curr Genet 17: 77–79) was used.

The transformation of the plasmid in potato plant was carried out using *Agrobacterium tumefaciens* strain LBA4404 (Bevan (1984) Nucl. Acids Res 12: 8711–8720).

3. Transformation of *Agrobacterium tumefaciens*

The transfer of the DNA in the Agrobacteria was carried out by direct transformation by the method of Höfgen & Willmitzer (1988, Nucleic Acids Res 16: 9877). The plasmid DNA of the transformed Agrobacterium was isolated in accordance with the method of Birnboim and Doly (1979) (Nucl Acids Res 7: 1513–1523) and was analysed by gel electrophoresis after suitable restriction cleavage.

4. Plant transformation

Ten small leaves, wounded with a scalpel, of a sterile potato culture were placed in 10 ml of MS medium with 2% sucrose containing 30–50 μl of an *Agrobacterium tumefaciens* overnight culture grown under selection. After 3–5 minutes gentle shaking, the leaves were laid out on MS medium of 1.6% glucose, 2 mg/l of zeatin ribose, 0.02 mg/l of naphthylacetic acid, 0.02 mg/l of gibberellic acid, 500 mg/l of claforan, 50 mg/l of kanamycin and 0.8% bacto agar. After incubation for one week at 25° C. and 3000 lux, the claforan concentration in the medium was reduced by half.

Deposits

The following plasmids and yeast strains were deposited at the Deutschen Sammlung yon Mikroorganismen (DSM) in Braunschweig, Germany on the 12.06.1992 (deposit number):

| Plasmid | pSK-S21 | (DSM 7115) |
|---|---|---|
| Yeast strain | YSH 2.64-1A-SUSY | (DSM 7106) |
| Yeast strain | YSH 2.64-1A-INV | (DSM 7105) |

Description of the Figures

FIG. 1

Time pattern of the uptake of sucrose in yeast cells. "pmol/mg cells"=amount of the $^{14}$C-labelled sucrose in pmol taken up in relation to the moisture weight of the yeast cells per mg; "112"=starting strain (without transporter); "+Glucose"=pre-incubation of the cells in a medium of 10 mM glucose; "–Glucose"=no pre-incubation of the cells; "2.5 μMCCCP"=coincubation with the inhibitor, carbonyl cyanide m-chlorophenylhydrazone (CCCP) in a concentration of 2.5 μM; "500 μMPCMBS"=coincubation with the inhibitor p-chloromercuribenzenesulfonic acid (PCMBS) in a concentration of 500 μM; "10 μM Antimycin"=coincubation with the inhibitor antimycin in a concentration of 10 μM.

FIG. 2

Cloning of the plasmid pMA5-INV. Shows the insertion of 2.4 kb size HindIII Fragment from pSEYC 306-1 in pMA5–10

FIG. 3 shows the plasmid pBinAR-S21.

| In this:: | |
|---|---|
| CaMV 35S promoter: | promoter of the gene for the 35S RNA of the cauliflower mosaic virus |
| A: | coding region of the sucrose transporter in spinach, orientation in the reading direction |
| OCS: | terminator of the octopine synthase gene from *Agrobacterium tumefaciens* |
| SmaI, NotI, BamHI: | Cleavage positions of restriction enzymes |

FIG. 4 shows the plasmid pBinAR-P62-anti.

| In this:: | |
|---|---|
| CaMV 35S promoter: | promoter of the gene for the 35S RNA of the cauliflower mosaic virus |
| OCS: | terminator of the octopine synthase gene from *Agrobacterium tumefaciens* |
| SmaI, SacI, BamHI, XbaI: | Cleavage positions of restriction enzymes |

FIG. 5

Content of various carbohydrates in leaves of BinAR-P62-anti transformands.

| In this | |
|---|---|
| fru: | fructose |
| suc: | sucrose |
| sta: | starch |
| control: | untransformed starting plants |
| sp-5 to sp-43: | transformands with individual numbers |

FIG. 6

Efflux of carbohydrates from petioles of BinAR-P62-anti transformands

| wt: | Wild type |
|---|---|
| sp-5 to sp-43: | transformands with individual numbers |

The following examples describe the preparation of the yeast strains, the identification as well as the function and use of a plant sucrose transporter.

EXAMPLE 1

Preparation of the yeast strains YSH 2.64-1A-SUSY and YSH 2.64-1A-INV

The yeast strain YSH 2.64-1A has the features suc2-, mal0, leu2, trp1 (Gozalbo & Hohmann, 1990, Curr Genet 17: 77–79). In order to introduce sucrose cleaving enzymatic activity in this strain, it was transformed with the integrative plasmid YIplac128A2-SUSY, that contains the coding region of the sucrose synthase from potato as a fusion to the promoter of the gene for alcohol dehydrogenase from yeast. The plasmid YIplac 128A2-SUSY was prepared as follows. The plasmid YIplac128 (Gietz & Sugino, 1988, Gene 74: 527–534) was shortened by cleavage with PstI and EcoRI, degradation and/or filling in of overhanging single strands and ligation in the region of the polylinker. In the remaining SphI cleavage position, a 728 bp cassette was inserted with the promoter of alcohol dehydrogenase from the plasmid pVT102U (Vernet et al., 1987, Gene 52: 225–233). In this way YIplac128A2 was obtained. The coding region of the sucrose synthase was amplified by polymerase chain reaction with the oligonucleotides

SUSY1
(GAGAGAGGATCCTGCAATGGCTGAACGTGTTTTGACTCGTG)

and

SUSY2
(GAGAGAGGATCCTTCATTCACTCAGCAGCCAATGGAACAGCT)

to a lambda clone of sucrose synthase from potato (Salanoubat & Belliard, 1987, Gene 60: 47–56). From the product, the coding region was prepared as BamHI fragment and inserted in the BamHI cleavage site of the polylinker of the cassette. The yeast strain YSH 2.64-1A was transformed with the so prepared plasmid YIplac128A2-SUSY. Since the plasmid does not carry the 2µ region, it cannot be autonomically replicated in yeast. Therefore such transformands only acquire leucine auxotrophy, which at least partially chromosomally integrate the plasmid-DNA.

Leucine autotroph colonies were analysed for expression of the sucrose synthase gene. For this, cells of a 5 ml liquid culture were decomposed by addition of glass pearls with vigorous shaking, and then, after centrifuging, total protein from the supernatant was added for an enzyme activity measurement. The activity of the expressed sucrose synthase contains 25 mU/mg protein.

In a similar manner an invertase activity was introduced in the yeast strain YSH 2.64-1A, in which by help of the plasmid YIplac128A1-INV, a gene for a cytosolic, noncleavable invertase was chromosomally integrated in the yeast genome. YIplac128A1-INV contains instead of the coding region for sucrose synthase, an invertase gene, which lacks the signal sequence for export of the gene product. The precursor of the plasmid is the plasmid YIplac128A1, which differs from YIplac128A2 in the orientation of the polylinker in the cassette with the promoter of the alcohol dehydrogenase gene. The cassette for this plasmid derives from the plasmid pVT100U (Vernet et al., 1987, Gene 52: 225–233). The coding region of the invertase was obtained on the DNA of the suc2 gene by polymerase chain reaction with the oligonucleotides INV3 (GAGCTGCAGATGGCAAAC-GAAACTAGCGATAGACCTTTGGTCACA) and INV4 (GAGACTAGTTTATAACCTCTATTTTACT-TCCCTTACTTGGAA). The coding region was ligated as PstI/SpeI fragment in the linearised vector YIplac128A1den using PstI and XbaI. A test of the enzymatic activity of the invertase activity expressed in the yeast cells, resulted in an enzyme activity of 68 mU/mg total protein from yeast cells.

EXAMPLE 2

Cloning of the cDNA plant sucrose transporter

From polyadenylated RNA from leaf tissue of growing spinach and potato plants, a library of the cDNA in the phage Lambda ZAP II library was prepared. From 500,000 Pfu, the phage DNA was prepared and purified using a caesium chloride sarcosyl gradient. After cleaving the phage DNA with the enzyme NotI, insertions from the size regions above and below 1.5 kbp were prepared on a 1% agarose gel and ligated in the NotI cleavage sites of the expressions vector YEplac112A1NE. The vector is a derivative of the vector YEplac 112 (Gozalbo & Hohmann, 1990, Curr Genet 17: 77–79), with which, as described in Example 1, the polylinker was exchanged with a cassette with the promoter of the alcohol dehydrogenase gene. The polylinker of the cassette was again removed by cleavage with the enzymes PstI and XbaI and replaced by a double stranded oligonucleotide that introduces a NotI and EcoRI cleavage site (Sequence: GATCCGCGGCCGCCCGGAATTCTCTA-GACTGCA).

Approximately 90,000 clones for the size region below 1.5 kbp and approximately 40,000 clones for the size region above 1.5 kbp were obtained by transformation in E. coli. From these, plasmid DNA was prepared. 2 µg DNA was transformed fourteen times in the yeast strain YSH2.64-1A suc-.susy. Transformands were grown on a medium containing 2% glucose, and five to ten thousand of each were washed off with agar plate liquid medium and plated out on sucrose containing medium. Those colonies, which could be grown faster were further analysed. The insertion in the vector YEplac112A1NE of transformands S21 or P62 (YEplac112A1NE-S21) were sequenced. The sequences are given above

EXAMPLE 3

Analysis of sucrose metabolising yeast transformands

The yeast transformand YEplac112A1NE-S21, corresponding to that obtained in Example 2, was grown in liquid medium until the culture had reached the logarithmic phase. After centrifuging the culture, the cells were subjected to a pre-incubation for 5 minutes in a glucose containing medium and then taken up in a medium containing $^{14}$C-labelled sucrose. The uptake of the labelled sucrose was measured by the process described by Cirillo (1989, Meth Enzymol 174: 617–622). The uptake of the labelled sucrose without preincubation with glucose was compared with that with co-incubation with the inhibitors carbonyl cyanide m-chlorophenylhydrazone (CCCP), p-chloromercuribenzenesulfonic acid (PCMBS) and antimycin. The time pattern is shown in FIG. 1. The calculated reduction of the sucrose uptake by the inhibitors is shown in table I. A competition experiment with various sugars as competitor for the labelled sucrose, from which the specificity of the transporter can be read off, is shown in table II.

Analogous measurements were carried out with the yeast strain YEplac112A1NE-P62. These gave similar results.

EXAMPLE 4

Figure 2:
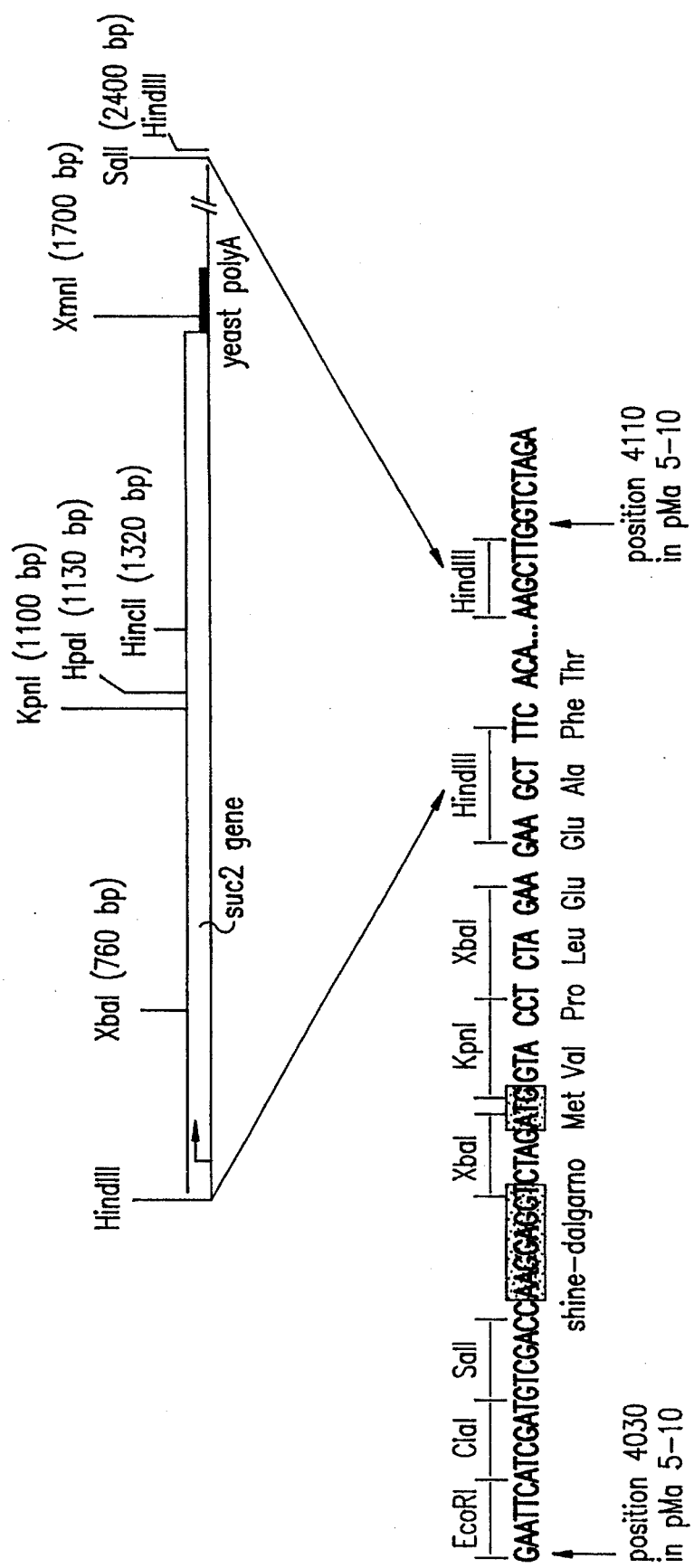
FIG. 2 shows the cloning of the plasmid pMA5-INV.

Transformation of bacterial strains with DNA sequences for expression of a sucrose transporter activity In order to be able to metabolise taken-up sucrose, bacterial cells are needed which have an enzymatic activity for cleavage of the monosaccharide. To introduce such an activity, bacteria were transformed by the plasmid pMA5-INV and tested for invertase activity. The plasmid pMA5-INV was prepared as follows. The plasmid pMA5–10 (Stanssens et al., 1989, Nucl Acids Res 17: 4441–4454) was linearised at the HindIII cleavage site of the polylinker. The 2.4 kb HindIII fragment of the plasmid pSEYC306-1 (Taussig & Carlson, 1983, Nucl Acids Res 11: 1943–1954) was cloned in the HindIII cleavage site. The corresponding cutout of the plasmid is shown in FIG. 2. The enzymatic activity of the invertase in bacteria cells, transformed with the plasmid pMA5-INV was determined in a gel electrophoresis activity test, in known manner. The possibility of the formation of a functional sucrose transporter though expression of a plant cDNA in bacteria cells was tested by transformation of *E. coli* with the plasmid pSK-S21. The plasmid is described Example 3. After transformation of bacteria cells with pSK-S21, tests for sucrose uptake were carried out.

EXAMPLE 5

Figure 3:
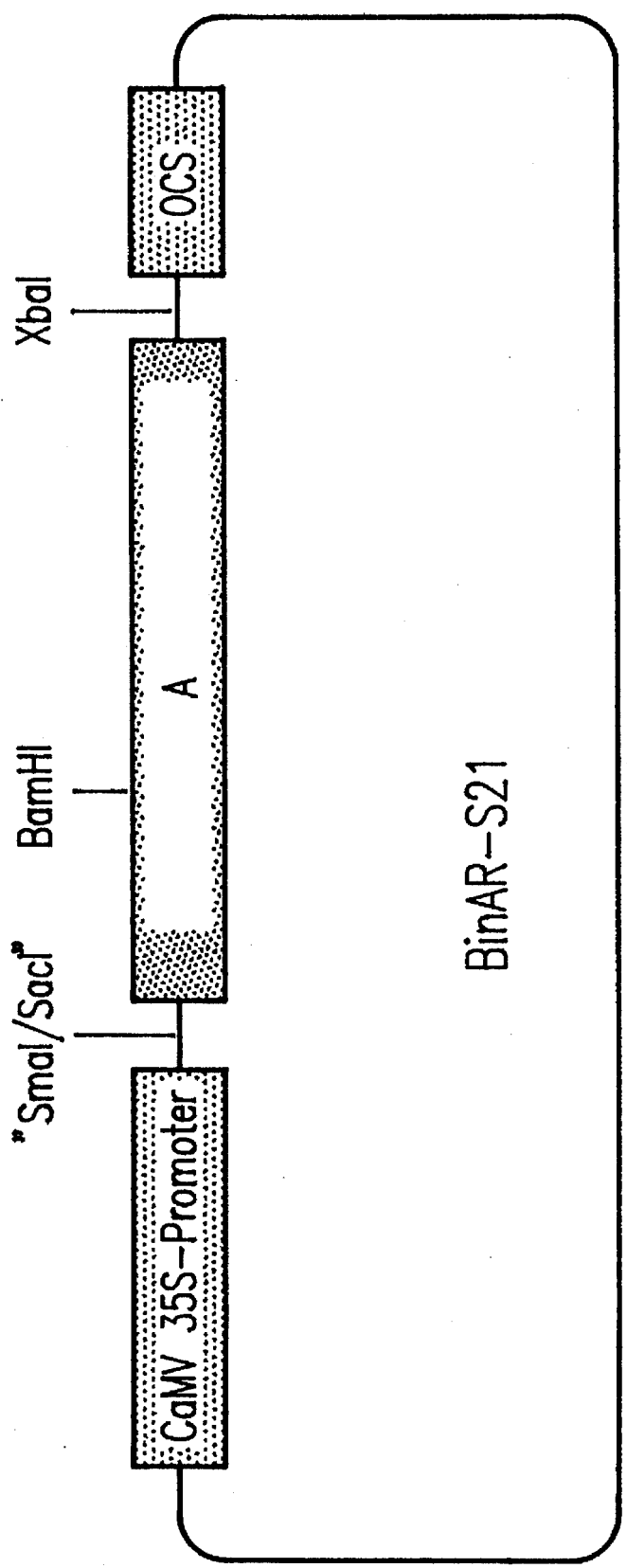
FIG. 3 is a diagram of the plasmid pBinAR-S21.
Figure 4:
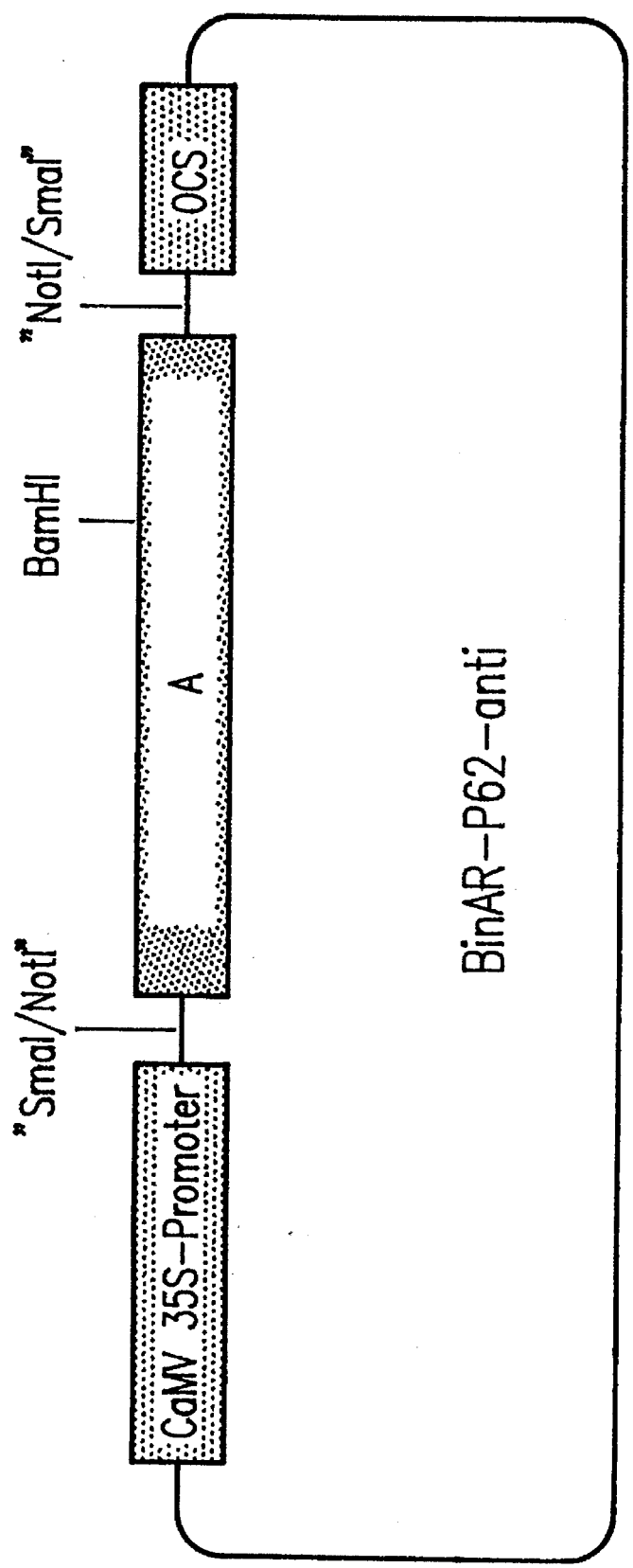
FIG. 4 is a diagram of the plasmid pBinAR-P62 -anti.

Transformation of plants with a construct for over-expression of the coding region of the sucrose transporter From the vectors YEplac 112A1NE-S21 and YEplac 112A1NE-P62, which contain, as inserts, the cDNA for the sucrose transporter from spinach and/or potato (see Examples 2 and 3), the inserts after NotI cleavage were isolated and ligated in the NotI cleavage site of the plasmids pBluescript-SK (pSK-S21 and/or pSK-P62). For pSK-S21, the insert was prepared as a SacI/XbaI fragment and cloned, after filling in the overhanging single strand-DNA, in the "sense" orientation in pBinAR (Höfgen & Willmitzer, 1990, Plant Sci 66: 221–230) which was previously cleaved with the enzymes SmaI and XbaI. The resulting plasmid pBinAR-S21 (see FIG. 3) can be inserted for transformation of plants in order to over-express the sucrose transporter. For pSK-P62, the insert was isolated as a 1.7 kbp NotI fragment and cloned in an "antisense" orientation in the SmaI cleavage site of the binary vector pBinAR, resulting in pBinAR-P62-anti (see FIG. 4). This plasmid is suitable for transformation of plants with the aim of "antisense" inhibition of the expression of the sucrose transporter.

Transformation Agrobacteria were then used for infection of leaf segments of tobacco and potato.

In ten independently obtained transformands, in which the presence of the intact, non-rearranged chimeric gene was demonstrated by Southern blot analysis, changes in sucrose, hexose and starch content were respectively tested.

Figure 5:
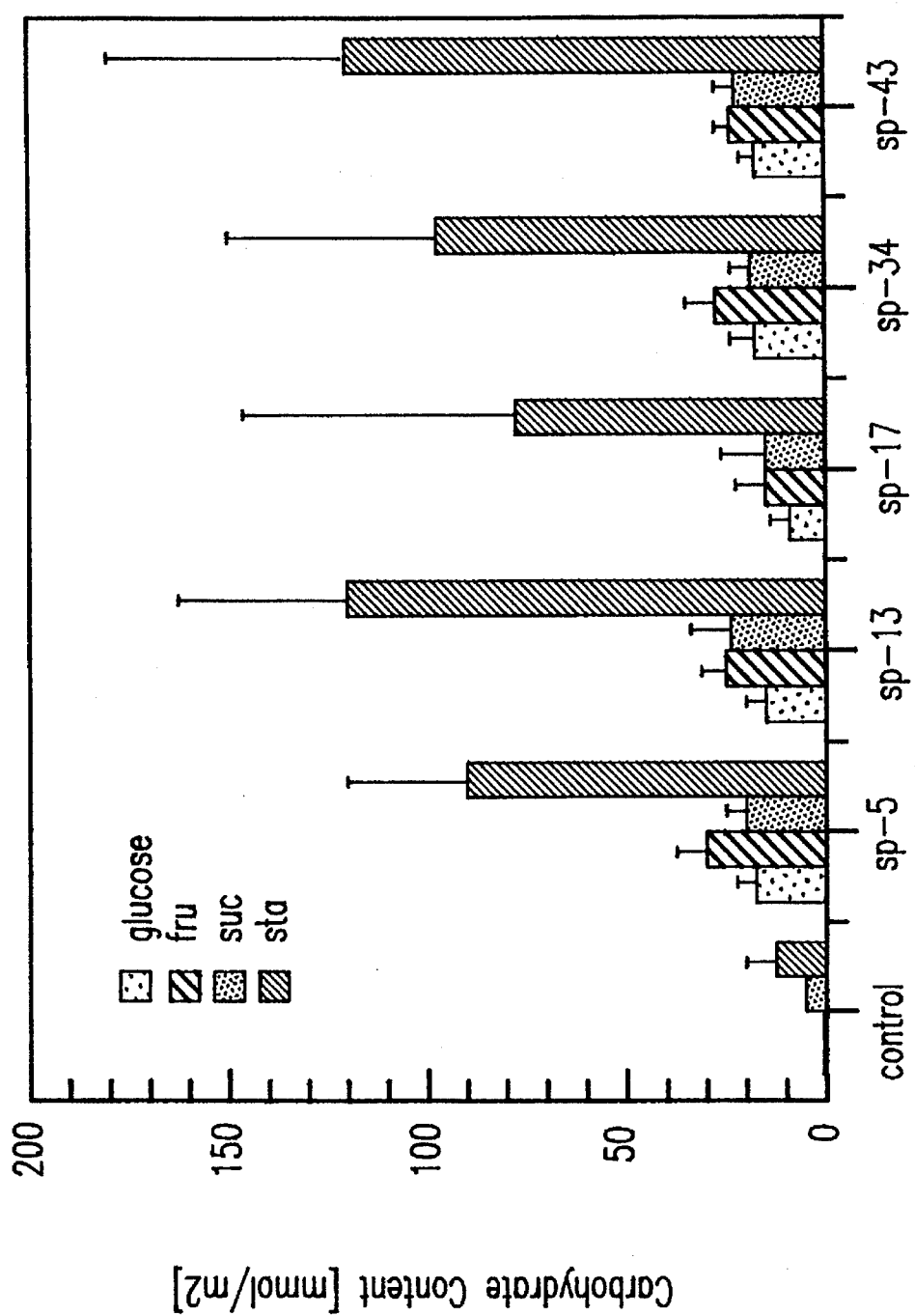
FIG. 5 is a graph of the content of various carbohydrates in the leaves of plants transformed with the plasmid BinAR-P62-anti.
Figure 6:
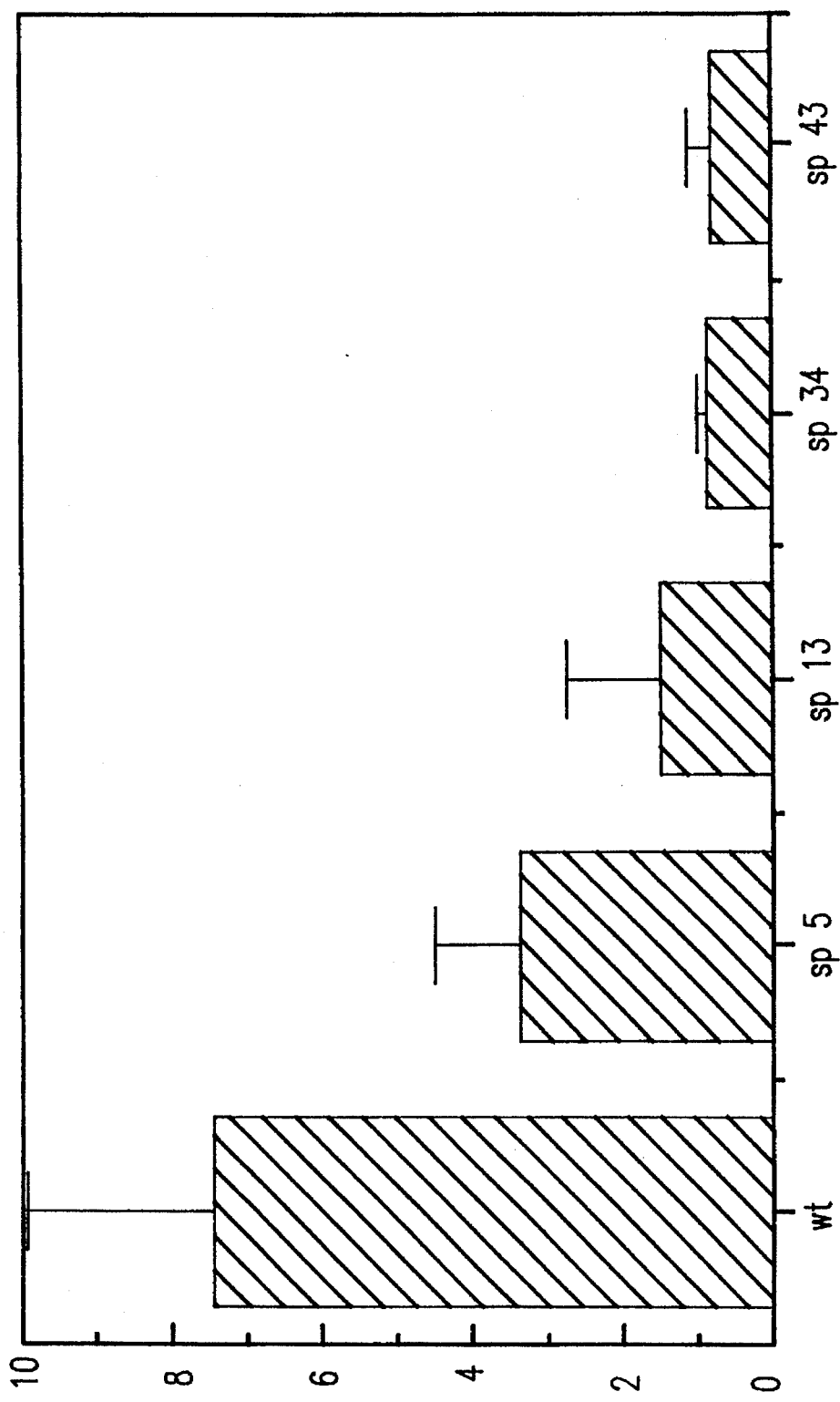
FIG. 6 is a graph of the efflux of carbohydrates from the petioles of plants transformed with the plasmid BinARP62-anti.

Transformands, which contain the T-DNA from pBinAR-P62-anti, showed a strongly increased concentration of starches, hexoses and sucrose in the leaves (see FIG. 5). The efflux of carbohydrate from the petioles taken from the plants is greatly reduced in aqueous medium (see FIG. 6). From these data, the significance of the sucrose transporter for the transport away of the photoassimilate from the photosynthetically active organs is clearly seen. Since an inhibition of the activity of the transporter limits the transport away of carbohydrates, this results from a lowering of the transfer of photoassimilates to storage organs in the case of an over-expression, for example using the plasmid pBinAR-S21. Tobacco plants, in which the T-DNA from pBinAR-S21 has been integrated, show further a reduced apical dominance, i.e. they show a bushy growth. Such a phenotypical change is, for example, very desirable in tomato plants. The plasmid pBinAR-S21 with the DNA sequence (Seq. ID No. 1) of the invention is therefore suited for the modification of plants with the purpose of improving important breeding characteristics such as bushy growth.

TABLE I

| Inhibitor | sucrose transport* (%) |
|---|---|
| Control | 100 |
| 0.5 µM CCCP | 65 |
| 2.5 µM CCCP | 21 |
| 25 µM PCMBS | 73 |
| 100 µM PCMBS | 21 |
| 25 µM 2,4-DNP | 61 |
| 100 µM 2,4-DNP | 9 |
| 1 mM sodium arsenate | 34 |
| 10 µM antimycin A | 59 |
| 1 m cAMP | 102 |

CCCP = carbonyl cyanide m-chlorophenylhydrazone
PCMBS = p-chloromercuribenzenesulfonic acid
2,4-DNP = 2,4-dinitrophenol
*= in relation to Y Eplac 112 A1NE-S21 (control)

TABLE II

| Competitor | sucrose transport* (%) |
|---|---|
| Control | 100 |
| 2 mM sucrose | 28 |
| 2 mM maltose | 58 |
| 10 mM maltose | 37 |
| 2 mM phenylglucoside | 7 |
| 2 mM phloridzin | 16 |
| 2 mM lactose | 91 |
| 10 mM palatinose | 102 |
| 10 mM trehalose | 103 |

*= in relation to YEplac 112 A1NE - S21 (control)

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 1969 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Spinacia oleracea ( i x ) FEATURE:
    ( A ) NAME/KEY: CDS
    ( B ) LOCATION: 70..1644
    ( D ) OTHER INFORMATION: /note="Sucrose-Transporter"

( x i ) SEQUENCE DESCRIPTION: SEQ ID NO:1:

```
AAAACACAC   ACCCAAAAAA  AAAACACTAC  GACTATTTCA  AAAAAAACAT  TGTTACTAGA           60

AATCTTATT ATG GCA GGA AGA AAT ATA AAA AAT GGT GAA AAT AAC AAG                   108
          Met Ala Gly Arg Asn Ile Lys Asn Gly Glu Asn Asn Lys
           1               5                  10

ATT GCG GGT TCT TCT CTT CAC TTA GAG AAG AAC CCA ACA ACT CCC CCC                 156
Ile Ala Gly Ser Ser Leu His Leu Glu Lys Asn Pro Thr Thr Pro Pro
         15              20                  25

GAG GCC GAG GCT ACC TTA AAG AAG CTC GGC CTC GTG GCT TCA GTA GCG                 204
Glu Ala Glu Ala Thr Leu Lys Lys Leu Gly Leu Val Ala Ser Val Ala
 30              35                  40                      45

GCC GGG GTT CAG TTC GGG TGG GCT TTA CAG CTC TCC CTA CTG ACC CCG                 252
Ala Gly Val Gln Phe Gly Trp Ala Leu Gln Leu Ser Leu Leu Thr Pro
                 50                  55                  60

TAC GTC CAA CTA CTG GGC ATT CCC CAC ACT TGG GCC GCC TAC ATC TGG                 300
Tyr Val Gln Leu Leu Gly Ile Pro His Thr Trp Ala Ala Tyr Ile Trp
                 65              70                  75

TTG TGC GGC CCA ATC TCG GGG ATG ATT GTC CAG CCA TTG GTC GGG TAC                 348
Leu Cys Gly Pro Ile Ser Gly Met Ile Val Gln Pro Leu Val Gly Tyr
             80                  85                  90

TAT AGT GAC CGG TGC ACC TCC CGC TTC GGC CGA CGT CGC CCC TTC ATT                 396
Tyr Ser Asp Arg Cys Thr Ser Arg Phe Gly Arg Arg Arg Pro Phe Ile
     95                 100                 105

GCA GCA GGG GCG GCT CTA GTG GCC GTA GCG GTG GGG CTA ATC GGA TTC                 444
Ala Ala Gly Ala Ala Leu Val Ala Val Ala Val Gly Leu Ile Gly Phe
110                 115                 120                 125

GCC GCC GAT ATC GGC GCA GCG TCG GGT GAT CCA ACG GGA AAC GTG GCA                 492
Ala Ala Asp Ile Gly Ala Ala Ser Gly Asp Pro Thr Gly Asn Val Ala
                 130                 135                 140

AAA CCC CGG GCC ATC GCG GTG TTT GTG GTC GGG TTT TGG ATC CTC GAC                 540
Lys Pro Arg Ala Ile Ala Val Phe Val Val Gly Phe Trp Ile Leu Asp
                 145             150                 155

GTG GCT AAC AAC ACC CTG CAA GGC CCA TGC AGG GCG TTG TTA GCA GAC                 588
Val Ala Asn Asn Thr Leu Gln Gly Pro Cys Arg Ala Leu Leu Ala Asp
        160                 165                 170

ATG GCC GCC GGG TCG CAA ACC AAA ACC CGG TAC GCT AAC GCC TTC TTC                 636
Met Ala Ala Gly Ser Gln Thr Lys Thr Arg Tyr Ala Asn Ala Phe Phe
        175                 180                 185

TCC TTC TTC ATG GCG TTA GGA AAC ATC GGA GGG TAC GCC GCC GGT TCA                 684
Ser Phe Phe Met Ala Leu Gly Asn Ile Gly Gly Tyr Ala Ala Gly Ser
```

-continued

| | | | | | | | | | | | | | | | | |
|---|---|---|---|---|---|---|---|---|---|---|---|---|---|---|---|---|
| 190 | | | | | 195 | | | | | 200 | | | | | 205 | |

| TAC | AGC | CGC | CTC | TAC | ACG | GTG | TTC | CCC | TTT | ACC | AAA | ACC | GCC | GCC | TGC | 732 |
|---|---|---|---|---|---|---|---|---|---|---|---|---|---|---|---|---|
| Tyr | Ser | Arg | Leu | Tyr 210 | Thr | Val | Phe | Pro | Phe 215 | Thr | Lys | Thr | Ala | Ala 220 | Cys | |

| GAC | GTC | TAC | TGC | GCC | AAT | CTA | AAA | TCC | TGC | TTC | TTC | ATC | TCC | ATC | ACA | 780 |
| Asp | Val | Tyr | Cys 225 | Ala | Asn | Leu | Lys | Ser 230 | Cys | Phe | Phe | Ile | Ser 235 | Ile | Thr | |

| CTC | CTA | ATC | GTC | CTC | ACA | ATC | CTA | GCA | CTT | TCC | GTC | GTA | AAA | GAG | CGT | 828 |
| Leu | Leu | Ile 240 | Val | Leu | Thr | Ile | Leu 245 | Ala | Leu | Ser | Val | Val 250 | Lys | Glu | Arg | |

| CAA | ATC | ACA | ATC | GAC | GAA | ATC | CAA | GAA | GAA | GAA | GAC | TTA | AAA | AAC | AGA | 876 |
| Gln | Ile | Thr 255 | Ile | Asp | Glu | Ile | Gln 260 | Glu | Glu | Glu | Asp | Leu 265 | Lys | Asn | Arg | |

| AAC | AAT | AGC | AGC | GGT | TGT | GCA | AGA | CTA | CCG | TTC | TTC | GGA | CAA | TTA | ATA | 924 |
| Asn 270 | Asn | Ser | Ser | Gly | Cys 275 | Ala | Arg | Leu | Pro | Phe 280 | Phe | Gly | Gln | Leu | Ile 285 | |

| GGC | GCT | CTC | AAA | GAT | CTA | CCA | AAA | CCA | ATG | CTA | ATC | CTA | TTA | CTA | GTA | 972 |
| Gly | Ala | Leu | Lys | Asp 290 | Leu | Pro | Lys | Pro | Met 295 | Leu | Ile | Leu | Leu 300 | Leu | Val | |

| ACA | GCC | CTA | AAT | TGG | ATC | GCA | TGG | TTT | CCA | TTC | TTG | TTG | TTC | GAT | ACT | 1020 |
| Thr | Ala | Leu | Asn 305 | Trp | Ile | Ala | Trp | Phe 310 | Pro | Phe | Leu | Leu | Phe 315 | Asp | Thr | |

| GAT | TGG | ATG | GGT | AAA | GAA | GTG | TAC | GGT | GGT | ACA | GTC | GGA | GAA | GGT | AAA | 1068 |
| Asp | Trp | Met 320 | Gly | Lys | Glu | Val | Tyr 325 | Gly | Gly | Thr | Val | Gly 330 | Glu | Gly | Lys | |

| TTG | TAC | GAC | CAA | GGA | GTT | CAT | GCC | GGT | GCC | TTA | GGT | CTG | ATG | ATT | AAC | 1116 |
| Leu | Tyr 335 | Asp | Gln | Gly | Val | His 340 | Ala | Gly | Ala | Leu | Gly 345 | Leu | Met | Ile | Asn | |

| TCC | GTT | GTC | TTA | GGT | GTT | ATG | TCG | TTG | AGT | ATT | GAA | GGT | TTG | GCT | CGT | 1164 |
| Ser 350 | Val | Val | Leu | Gly | Val 355 | Met | Ser | Leu | Ser | Ile 360 | Glu | Gly | Leu | Ala | Arg 365 | |

| ATG | GTA | GGC | GGT | GCT | AAA | AGG | TTA | TGG | GGA | ATT | GTC | AAT | ATT | ATT | CTT | 1212 |
| Met | Val | Gly | Gly | Ala 370 | Lys | Arg | Leu | Trp | Gly 375 | Ile | Val | Asn | Ile | Ile 380 | Leu | |

| GCT | GTT | TGT | TTA | GCT | ATG | ACG | GTG | TTA | GTT | ACT | AAG | TCC | GCC | GAA | CAC | 1260 |
| Ala | Val | Cys | Leu 385 | Ala | Met | Thr | Val | Leu 390 | Val | Thr | Lys | Ser | Ala 395 | Glu | His | |

| TTC | CGT | GAT | AGC | CAC | CAT | ATT | ATG | GGC | TCC | GCC | GTC | CCT | CCG | CCG | CCG | 1308 |
| Phe | Arg | Asp | Ser 400 | His | His | Ile | Met | Gly 405 | Ser | Ala | Val | Pro | Pro 410 | Pro | Pro | |

| CCT | GCT | GGT | GTT | AAG | GGT | GGC | GCT | TTG | GCT | ATC | TTT | GCC | GTT | CTT | GGT | 1356 |
| Pro | Ala | Gly 415 | Val | Lys | Gly | Gly | Ala 420 | Leu | Ala | Ile | Phe | Ala 425 | Val | Leu | Gly | |

| ATC | CCT | CTT | GCG | ATC | ACT | TTC | AGT | ATT | CCT | TTG | GCC | TTG | GCG | TCA | ATC | 1404 |
| Ile | Pro | Leu | Ala 430 | Ile | Thr | Phe | Ser | Ile 435 | Pro | Leu | Ala | Leu | Ala 440 | Ser | Ile 445 | |

| TTT | TCA | GCA | TCT | TCC | GGT | TCA | GGA | CAA | GGT | CTT | TCT | CTA | GGA | GTT | CTC | 1452 |
| Phe | Ser | Ala | Ser | Ser 450 | Gly | Ser | Gly | Gln | Gly 455 | Leu | Ser | Leu | Gly | Val 460 | Leu | |

| AAC | CTC | GCC | ATC | GTT | GTA | CCC | CAG | ATG | TTT | GTG | TCG | GTA | ACA | AGT | GGG | 1500 |
| Asn | Leu | Ala | Ile 465 | Val | Val | Pro | Gln | Met 470 | Phe | Val | Ser | Val | Thr 475 | Ser | Gly | |

| CCA | TGG | GAT | GCA | ATG | TTT | GGT | GGA | GGA | AAT | TTG | CCA | GCA | TTC | GTG | GTG | 1548 |
| Pro | Trp | Asp 480 | Ala | Met | Phe | Gly | Gly 485 | Gly | Asn | Leu | Pro | Ala 490 | Phe | Val | Val | |

| GGA | GCT | GTA | GCA | GCA | ACA | GCC | AGT | GCA | GTT | CTT | TCA | TTT | ACA | TTG | TTG | 1596 |
| Gly | Ala | Val | Ala 495 | Ala | Thr | Ala | Ser | Ala 500 | Val | Leu | Ser | Phe 505 | Thr | Leu | Leu | |

| CCT | TCT | CCA | CCC | CCT | GAA | GCT | AAA | ATT | GGT | GGG | TCC | ATG | GGT | GGT | CAT | 1644 |
| Pro | Ser | Pro | Pro | Pro | Glu | Ala | Lys | Ile | Gly | Gly | Ser | Met | Gly | Gly | His | |

|   |   |   |   |   |
|---|---|---|---|---|
| 510 | 515 | 520 | 525 | |
| TAAGAAATTT | AATACTACTC | CGTACAATTT | AAACCCAAAT TAAAAATGAA AATGAAAATT | 1704 |
| TTTAACCCAT | GTTCGTTACG | TTGTAATTAG | AGAGAAAAAT GATATATTGA ACGAAGCCGT | 1764 |
| TAATTTATGC | TCCGTTCATC | TTGTAATTCT | TTTTCTCTCT GCTTTTTTTT TTTTTTTTA | 1824 |
| ACGCGACGTG | TTTTGAGAT | AAGGAAGGGC | TAGATCGAGG ATGGGGGAAT TGGCAAGAAA | 1884 |
| TTGCTCGGGT | ATAAATATTT | ATCCCTCTTT | GTAATTTTCA GTAACATTTA ATAGCCAGAA | 1944 |
| ATCAAAAAGT | CAAGAAAAAT | CGAAA | | 1969 |

( 2 ) INFORMATION FOR SEQ ID NO:2:

( i ) SEQUENCE CHARACTERISTICS:
       ( A ) LENGTH: 525 amino acids
       ( B ) TYPE: amino acid
       ( D ) TOPOLOGY: linear ( i i ) MOLECULE TYPE: protein ( x i ) SEQUENCE DESCRIPTION: SEQ ID NO:2:

```
Met Ala Gly Arg Asn Ile Lys Asn Gly Glu Asn Asn Lys Ile Ala Gly
 1               5                  10                  15

Ser Ser Leu His Leu Glu Lys Asn Pro Thr Thr Pro Pro Glu Ala Glu
            20                  25                  30

Ala Thr Leu Lys Lys Leu Gly Leu Val Ala Ser Val Ala Ala Gly Val
        35                  40                  45

Gln Phe Gly Trp Ala Leu Gln Leu Ser Leu Leu Thr Pro Tyr Val Gln
    50                  55                  60

Leu Leu Gly Ile Pro His Thr Trp Ala Ala Tyr Ile Trp Leu Cys Gly
65                  70                  75                  80

Pro Ile Ser Gly Met Ile Val Gln Pro Leu Val Gly Tyr Tyr Ser Asp
                85                  90                  95

Arg Cys Thr Ser Arg Phe Gly Arg Arg Pro Phe Ile Ala Ala Gly
                100                 105                 110

Ala Ala Leu Val Ala Val Ala Val Gly Leu Ile Gly Phe Ala Ala Asp
            115                 120                 125

Ile Gly Ala Ala Ser Gly Asp Pro Thr Gly Asn Val Ala Lys Pro Arg
    130                 135                 140

Ala Ile Ala Val Phe Val Val Gly Phe Trp Ile Leu Asp Val Ala Asn
145                 150                 155                 160

Asn Thr Leu Gln Gly Pro Cys Arg Ala Leu Leu Ala Asp Met Ala Ala
                165                 170                 175

Gly Ser Gln Thr Lys Thr Arg Tyr Ala Asn Ala Phe Phe Ser Phe Phe
            180                 185                 190

Met Ala Leu Gly Asn Ile Gly Gly Tyr Ala Ala Gly Ser Tyr Ser Arg
        195                 200                 205

Leu Tyr Thr Val Phe Pro Phe Thr Lys Thr Ala Ala Cys Asp Val Tyr
    210                 215                 220

Cys Ala Asn Leu Lys Ser Cys Phe Phe Ile Ser Ile Thr Leu Leu Ile
225                 230                 235                 240

Val Leu Thr Ile Leu Ala Leu Ser Val Val Lys Glu Arg Gln Ile Thr
                245                 250                 255

Ile Asp Glu Ile Gln Glu Glu Glu Asp Leu Lys Asn Arg Asn Asn Ser
            260                 265                 270

Ser Gly Cys Ala Arg Leu Pro Phe Phe Gly Gln Leu Ile Gly Ala Leu
        275                 280                 285
```

| | | | | | | | | | | | | | | |
|---|---|---|---|---|---|---|---|---|---|---|---|---|---|---|
| Lys | Asp 290 | Leu | Pro | Lys | Pro 295 | Met | Leu | Ile | Leu | Leu 300 | Leu | Val | Thr | Ala | Leu |
| Asn 305 | Trp | Ile | Ala | Trp | Phe 310 | Pro | Phe | Leu | Leu | Phe 315 | Asp | Thr | Asp | Trp | Met 320 |
| Gly | Lys | Glu | Val | Tyr 325 | Gly | Gly | Thr | Val | Gly 330 | Glu | Gly | Lys | Leu | Tyr 335 | Asp |
| Gln | Gly | Val | His 340 | Ala | Gly | Ala | Leu | Gly 345 | Leu | Met | Ile | Asn | Ser 350 | Val | Val |
| Leu | Gly | Val 355 | Met | Ser | Leu | Ser | Ile 360 | Glu | Gly | Leu | Ala | Arg 365 | Met | Val | Gly |
| Gly | Ala 370 | Lys | Arg | Leu | Trp | Gly 375 | Ile | Val | Asn | Ile | Ile 380 | Leu | Ala | Val | Cys |
| Leu 385 | Ala | Met | Thr | Val | Leu 390 | Val | Thr | Lys | Ser | Ala 395 | Glu | His | Phe | Arg | Asp 400 |
| Ser | His | His | Ile | Met 405 | Gly | Ser | Ala | Val | Pro 410 | Pro | Pro | Pro | Ala 415 | Gly |
| Val | Lys | Gly | Gly 420 | Ala | Leu | Ala | Ile | Phe 425 | Ala | Val | Leu | Gly | Ile 430 | Pro | Leu |
| Ala | Ile | Thr 435 | Phe | Ser | Ile | Pro | Leu 440 | Ala | Leu | Ala | Ser | Ile 445 | Phe | Ser | Ala |
| Ser | Ser 450 | Gly | Ser | Gly | Gln | Gly 455 | Leu | Ser | Leu | Gly | Val 460 | Leu | Asn | Leu | Ala |
| Ile 465 | Val | Val | Pro | Gln | Met 470 | Phe | Val | Ser | Val | Thr 475 | Ser | Gly | Pro | Trp | Asp 480 |
| Ala | Met | Phe | Gly | Gly 485 | Gly | Asn | Leu | Pro | Ala 490 | Phe | Val | Val | Gly | Ala 495 | Val |
| Ala | Ala | Thr | Ala 500 | Ser | Ala | Val | Leu | Ser 505 | Phe | Thr | Leu | Leu | Pro 510 | Ser | Pro |
| Pro | Pro | Glu 515 | Ala | Lys | Ile | Gly | Gly 520 | Ser | Met | Gly | Gly 525 | His | | | |

( 2 ) INFORMATION FOR SEQ ID NO:3:

( i ) SEQUENCE CHARACTERISTICS:
        ( A ) LENGTH: 1773 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Solanum tuberosum ( i x ) FEATURE:
        ( A ) NAME/KEY: CDS
        ( B ) LOCATION: 5..1552
        ( D ) OTHER INFORMATION: /note="Sucrose-Transporter"

( x i ) SEQUENCE DESCRIPTION: SEQ ID NO:3:

```
AAAA ATG GAG AAT GGT ACA AAA AGA GAA GGT TTA GGG AAA CTT ACA GTT        49
     Met Glu Asn Gly Thr Lys Arg Glu Gly Leu Gly Lys Leu Thr Val
      1               5                  10                  15

TCA TCT TCT CTA CAA GTT GAA CAG CCT TTA GCA CCA TCA AAG CTA TGG        97
Ser Ser Ser Leu Gln Val Glu Gln Pro Leu Ala Pro Ser Lys Leu Trp
             20                  25                  30

AAA ATT ATA GTT GTA GCT TCC ATA GCT GCT GGT GTT CAA TTT GGT TGG       145
Lys Ile Ile Val Val Ala Ser Ile Ala Ala Gly Val Gln Phe Gly Trp
                 35                  40                  45

GCT CTT CAG CTC TCT TTG CTT ACA CCT TAT GTT CAA TTG CTC GGA ATT       193
Ala Leu Gln Leu Ser Leu Leu Thr Pro Tyr Val Gln Leu Leu Gly Ile
```

|  |  |  |  |  |  |  |  |  |  |  |  |  |  |  |  |
|---|---|---|---|---|---|---|---|---|---|---|---|---|---|---|---|
|  |  | 50 |  |  |  |  | 55 |  |  |  |  | 60 |  |  |  |

```
CCT  CAT  AAA  TTT  GCC  TCT  TTT  ATT  TGG  CTT  TGT  GGA  CCG  ATT  TCT  GGT     241
Pro  His  Lys  Phe  Ala  Ser  Phe  Ile  Trp  Leu  Cys  Gly  Pro  Ile  Ser  Gly
     65                       70                       75

ATG  ATT  GTT  CAG  CCA  GTT  GTC  GGC  TAC  TAC  AGT  GAT  AAT  TGC  TCC  TCC     289
Met  Ile  Val  Gln  Pro  Val  Val  Gly  Tyr  Tyr  Ser  Asp  Asn  Cys  Ser  Ser
 80                      85                       90                        95

CGT  TTC  GGT  CGC  CGC  CGG  CCA  TTC  ATT  GCC  GCC  GGA  GCT  GCA  CTT  GTT     337
Arg  Phe  Gly  Arg  Arg  Arg  Pro  Phe  Ile  Ala  Ala  Gly  Ala  Ala  Leu  Val
               100                      105                      110

ATG  ATT  GCG  GTT  TTC  CTC  ATC  GGA  TTC  GCC  GCC  GAC  CTT  GGT  CAC  GCC     385
Met  Ile  Ala  Val  Phe  Leu  Ile  Gly  Phe  Ala  Ala  Asp  Leu  Gly  His  Ala
               115                      120                      125

TCC  GGT  GAC  ACT  CTC  GGA  AAA  GGA  TTT  AAG  CCA  CGT  GCC  ATT  GCC  GTT     433
Ser  Gly  Asp  Thr  Leu  Gly  Lys  Gly  Phe  Lys  Pro  Arg  Ala  Ile  Ala  Val
               130                      135                      140

TTC  GTC  GTC  GGC  TTT  TGG  ATC  CTT  GAT  GTT  GCT  AAC  AAC  ATG  TTA  CAG     481
Phe  Val  Val  Gly  Phe  Trp  Ile  Leu  Asp  Val  Ala  Asn  Asn  Met  Leu  Gln
     145                      150                      155

GGC  CCA  TGC  AGA  GCA  CTA  CTG  GCT  GAT  CTC  TCC  GGC  GGA  AAA  TCC  GGC     529
Gly  Pro  Cys  Arg  Ala  Leu  Leu  Ala  Asp  Leu  Ser  Gly  Gly  Lys  Ser  Gly
160                      165                      170                      175

AGG  ATG  AGA  ACA  GCA  AAT  GCT  TTT  TTC  TCA  TTC  TTC  ATG  GCC  GTC  GGA     577
Arg  Met  Arg  Thr  Ala  Asn  Ala  Phe  Phe  Ser  Phe  Phe  Met  Ala  Val  Gly
                    180                      185                      190

AAC  ATT  CTG  GGG  TAC  GCC  GCC  GGT  TCA  TAT  TCT  CAC  CTC  TTT  AAA  GTA     625
Asn  Ile  Leu  Gly  Tyr  Ala  Ala  Gly  Ser  Tyr  Ser  His  Leu  Phe  Lys  Val
               195                      200                      205

TTC  CCC  TTC  TCA  AAA  ACC  AAA  GCC  TGC  GAC  ATG  TAC  TGC  GCA  AAT  CTG     673
Phe  Pro  Phe  Ser  Lys  Thr  Lys  Ala  Cys  Asp  Met  Tyr  Cys  Ala  Asn  Leu
          210                      215                      220

AAG  AGT  TGT  TTC  TTC  ATC  GCT  ATA  TTC  CTT  TTA  CTC  AGC  TTA  ACA  ACC     721
Lys  Ser  Cys  Phe  Phe  Ile  Ala  Ile  Phe  Leu  Leu  Leu  Ser  Leu  Thr  Thr
     225                      230                      235

ATA  GCC  TTA  ACC  TTA  GTC  CGG  GAA  AAC  GAG  CTC  CCG  GAG  AAA  GAC  GAG     769
Ile  Ala  Leu  Thr  Leu  Val  Arg  Glu  Asn  Glu  Leu  Pro  Glu  Lys  Asp  Glu
240                      245                      250                      255

CAA  GAA  ATC  GAC  GAG  AAA  TTA  GCC  GGC  GCC  GGA  AAA  TCG  AAA  GTA  CCG     817
Gln  Glu  Ile  Asp  Glu  Lys  Leu  Ala  Gly  Ala  Gly  Lys  Ser  Lys  Val  Pro
                    260                      265                      270

TTT  TTC  GGT  GAA  ATT  TTT  GGG  GCT  TTG  AAA  GAA  TTA  CCT  CGA  CCG  ATG     865
Phe  Phe  Gly  Glu  Ile  Phe  Gly  Ala  Leu  Lys  Glu  Leu  Pro  Arg  Pro  Met
               275                      280                      285

TGG  ATT  CTT  CTA  TTA  GTA  ACC  TGT  TTG  AAC  TGG  ATC  GCG  TGG  TTT  CCC     913
Trp  Ile  Leu  Leu  Leu  Val  Thr  Cys  Leu  Asn  Trp  Ile  Ala  Trp  Phe  Pro
          290                      295                      300

TTT  TTC  TTA  TAC  GAT  ACA  GAT  TGG  ATG  GCT  AAG  GAG  GTT  TTC  GGT  GGA     961
Phe  Phe  Leu  Tyr  Asp  Thr  Asp  Trp  Met  Ala  Lys  Glu  Val  Phe  Gly  Gly
     305                      310                      315

CAA  GTC  GGT  GAT  GCG  AGG  TTG  TAC  GAT  TTG  GGT  GTA  CGC  GCT  GGT  GCA    1009
Gln  Val  Gly  Asp  Ala  Arg  Leu  Tyr  Asp  Leu  Gly  Val  Arg  Ala  Gly  Ala
320                      325                      330                      335

ATG  GGA  TTA  CTG  TTG  CAA  TCT  GTG  GTT  CTA  GGG  TTT  ATG  TCA  CTT  GGG    1057
Met  Gly  Leu  Leu  Leu  Gln  Ser  Val  Val  Leu  Gly  Phe  Met  Ser  Leu  Gly
                    340                      345                      350

GTT  GAA  TTC  TTA  GGG  AAG  AAG  ATT  GGT  GGT  GCT  AAG  AGG  TTA  TGG  GGA    1105
Val  Glu  Phe  Leu  Gly  Lys  Lys  Ile  Gly  Gly  Ala  Lys  Arg  Leu  Trp  Gly
               355                      360                      365

ATT  TTG  AAC  TTT  GTT  TTG  GCT  ATT  TGC  TTG  GCT  ATG  ACC  ATT  TTG  GTC    1153
Ile  Leu  Asn  Phe  Val  Leu  Ala  Ile  Cys  Leu  Ala  Met  Thr  Ile  Leu  Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 370 |     |     |     |     |     | 375 |     |     |     |     | 380 |     |     |      |
| ACC | AAA | ATG | GCC | GAG | AAA | TCT | CGC | CAG | CAC | GAC | CCC | GCC | GGC | ACA | CTT | 1201 |
| Thr | Lys | Met | Ala | Glu | Lys | Ser | Arg | Gln | His | Asp | Pro | Ala | Gly | Thr | Leu |      |
|     | 385 |     |     |     | 390 |     |     |     |     | 395 |     |     |     |     |     |      |
| ATG | GGG | CCG | ACG | CCT | GGT | GTT | AAA | ATC | GGT | GCC | TTG | CTT | CTC | TTT | GCC | 1249 |
| Met | Gly | Pro | Thr | Pro | Gly | Val | Lys | Ile | Gly | Ala | Leu | Leu | Leu | Phe | Ala |      |
| 400 |     |     |     |     | 405 |     |     |     |     | 410 |     |     |     |     | 415 |      |
| GCC | CTT | GGT | ATT | CCT | CTT | GCG | GCA | ACT | TTT | AGT | ATT | CCA | TTT | GCT | TTG | 1297 |
| Ala | Leu | Gly | Ile | Pro | Leu | Ala | Ala | Thr | Phe | Ser | Ile | Pro | Phe | Ala | Leu |      |
|     |     |     |     | 420 |     |     |     |     | 425 |     |     |     |     | 430 |     |      |
| GCA | TCT | ATA | TTT | TCT | AGT | AAT | CGT | GGT | TCA | GGA | CAA | GGT | TTG | TCA | CTA | 1345 |
| Ala | Ser | Ile | Phe | Ser | Ser | Asn | Arg | Gly | Ser | Gly | Gln | Gly | Leu | Ser | Leu |      |
|     |     |     | 435 |     |     |     |     | 440 |     |     |     |     | 445 |     |     |      |
| GGA | GTG | CTC | AAT | CTT | GCA | ATT | GTT | GTA | CCA | CAG | ATG | TTG | GTG | TCA | CTA | 1393 |
| Gly | Val | Leu | Asn | Leu | Ala | Ile | Val | Val | Pro | Gln | Met | Leu | Val | Ser | Leu |      |
|     |     | 450 |     |     |     |     | 455 |     |     |     |     | 460 |     |     |     |      |
| GTA | GGA | GGG | CCA | TGG | GAT | GAT | TTG | TTT | GGA | GGA | GGA | AAC | TTG | CCT | GGA | 1441 |
| Val | Gly | Gly | Pro | Trp | Asp | Asp | Leu | Phe | Gly | Gly | Gly | Asn | Leu | Pro | Gly |      |
|     | 465 |     |     |     |     | 470 |     |     |     |     | 475 |     |     |     |     |      |
| TTT | GTA | GTT | GGA | GCA | GTT | GCA | GCT | GCC | GCG | AGC | GCT | GTT | TTA | GCA | CTC | 1489 |
| Phe | Val | Val | Gly | Ala | Val | Ala | Ala | Ala | Ala | Ser | Ala | Val | Leu | Ala | Leu |      |
| 480 |     |     |     |     | 485 |     |     |     |     | 490 |     |     |     |     | 495 |      |
| ACA | ATG | TTG | CCA | TCT | CCA | CCT | GCT | GAT | GCT | AAG | CCA | GCA | GTC | GCC | ATG | 1537 |
| Thr | Met | Leu | Pro | Ser | Pro | Pro | Ala | Asp | Ala | Lys | Pro | Ala | Val | Ala | Met |      |
|     |     |     |     | 500 |     |     |     |     | 505 |     |     |     |     | 510 |     |      |
| GGG | CTT | TCC | ATT | AAA | TAATTACAAA | AGAAGGAGAA | GAACAACTTT | TTTTTAATAT |  |  |  |  |  |  |  | 1592 |
| Gly | Leu | Ser | Ile | Lys |     |     |     |     |     |     |     |     |     |     |     |      |
|     |     |     |     | 515 |     |     |     |     |     |     |     |     |     |     |     |      |

```
TAGTACTTCT CTTTTGTAAA CTTTTTTTAT TTTAGAAAAC AAACATAACA TGGAGGCTAT     1652

CTTTACAAGT GGCATGTCCA TGTATCTTCC TTTTTTCATA AAGCTCTTTA GTGGAAGAAG     1712

AATTAGAGGA AGTTCCTTTT TAATTTCTTC CAAACAAATG GGGTATGTGT AGTTGTTTTC     1772

A                                                                     1773
```

(2) INFORMATION FOR SEQ ID NO:4:

(i) SEQUENCE CHARACTERISTICS:
        (A) LENGTH: 516 amino acids
        (B) TYPE: amino acid
        (D) TOPOLOGY: linear (ii) MOLECULE TYPE: protein (xi) SEQUENCE DESCRIPTION: SEQ ID NO:4:

| Met | Glu | Asn | Gly | Thr | Lys | Arg | Glu | Gly | Leu | Gly | Lys | Leu | Thr | Val | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Ser | Leu | Gln | Val | Glu | Gln | Pro | Leu | Ala | Pro | Ser | Lys | Leu | Trp | Lys |
|     |     |     | 20  |     |     |     |     | 25  |     |     |     |     | 30  |     |     |
| Ile | Ile | Val | Val | Ala | Ser | Ile | Ala | Ala | Gly | Val | Gln | Phe | Gly | Trp | Ala |
|     |     |     | 35  |     |     |     |     | 40  |     |     |     |     | 45  |     |     |
| Leu | Gln | Leu | Ser | Leu | Leu | Thr | Pro | Tyr | Val | Gln | Leu | Leu | Gly | Ile | Pro |
|     | 50  |     |     |     |     | 55  |     |     |     |     | 60  |     |     |     |     |
| His | Lys | Phe | Ala | Ser | Phe | Ile | Trp | Leu | Cys | Gly | Pro | Ile | Ser | Gly | Met |
| 65  |     |     |     |     | 70  |     |     |     |     | 75  |     |     |     |     | 80  |
| Ile | Val | Gln | Pro | Val | Val | Gly | Tyr | Tyr | Ser | Asp | Asn | Cys | Ser | Ser | Arg |
|     |     |     |     | 85  |     |     |     |     | 90  |     |     |     |     | 95  |     |
| Phe | Gly | Arg | Arg | Arg | Pro | Phe | Ile | Ala | Ala | Gly | Ala | Ala | Leu | Val | Met |
|     |     |     |     | 100 |     |     |     |     | 105 |     |     |     |     | 110 |     |
| Ile | Ala | Val | Phe | Leu | Ile | Gly | Phe | Ala | Ala | Asp | Leu | Gly | His | Ala | Ser |

|     |     |     | 115 |     |     | 120 |     |     |     |     | 125 |     |     |     |
| --- | --- | --- | --- | --- | --- | --- | --- | --- | --- | --- | --- | --- | --- | --- |
| Gly | Asp | Thr | Leu | Gly | Lys | Gly | Phe | Lys | Pro | Arg | Ala | Ile | Ala | Val | Phe |
|     | 130 |     |     |     |     | 135 |     |     |     |     | 140 |     |     |     |
| Val | Val | Gly | Phe | Trp | Ile | Leu | Asp | Val | Ala | Asn | Asn | Met | Leu | Gln | Gly |
| 145 |     |     |     |     | 150 |     |     |     |     | 155 |     |     |     |     | 160 |
| Pro | Cys | Arg | Ala | Leu | Leu | Ala | Asp | Leu | Ser | Gly | Gly | Lys | Ser | Gly | Arg |
|     |     |     |     | 165 |     |     |     |     | 170 |     |     |     |     | 175 |     |
| Met | Arg | Thr | Ala | Asn | Ala | Phe | Phe | Ser | Phe | Phe | Met | Ala | Val | Gly | Asn |
|     |     |     | 180 |     |     |     |     | 185 |     |     |     |     | 190 |     |     |
| Ile | Leu | Gly | Tyr | Ala | Ala | Gly | Ser | Tyr | Ser | His | Leu | Phe | Lys | Val | Phe |
|     |     | 195 |     |     |     |     | 200 |     |     |     |     | 205 |     |     |     |
| Pro | Phe | Ser | Lys | Thr | Lys | Ala | Cys | Asp | Met | Tyr | Cys | Ala | Asn | Leu | Lys |
|     | 210 |     |     |     |     | 215 |     |     |     |     | 220 |     |     |     |     |
| Ser | Cys | Phe | Phe | Ile | Ala | Ile | Phe | Leu | Leu | Leu | Ser | Leu | Thr | Thr | Ile |
| 225 |     |     |     |     | 230 |     |     |     |     | 235 |     |     |     |     | 240 |
| Ala | Leu | Thr | Leu | Val | Arg | Glu | Asn | Glu | Leu | Pro | Glu | Lys | Asp | Glu | Gln |
|     |     |     |     | 245 |     |     |     |     | 250 |     |     |     |     | 255 |     |
| Glu | Ile | Asp | Glu | Lys | Leu | Ala | Gly | Ala | Gly | Lys | Ser | Lys | Val | Pro | Phe |
|     |     |     | 260 |     |     |     |     | 265 |     |     |     |     | 270 |     |     |
| Phe | Gly | Glu | Ile | Phe | Gly | Ala | Leu | Lys | Glu | Leu | Pro | Arg | Pro | Met | Trp |
|     |     | 275 |     |     |     |     | 280 |     |     |     |     | 285 |     |     |     |
| Ile | Leu | Leu | Leu | Val | Thr | Cys | Leu | Asn | Trp | Ile | Ala | Trp | Phe | Pro | Phe |
|     | 290 |     |     |     |     | 295 |     |     |     |     | 300 |     |     |     |     |
| Phe | Leu | Tyr | Asp | Thr | Asp | Trp | Met | Ala | Lys | Glu | Val | Phe | Gly | Gly | Gln |
| 305 |     |     |     |     | 310 |     |     |     |     | 315 |     |     |     |     | 320 |
| Val | Gly | Asp | Ala | Arg | Leu | Tyr | Asp | Leu | Gly | Val | Arg | Ala | Gly | Ala | Met |
|     |     |     |     | 325 |     |     |     |     | 330 |     |     |     |     | 335 |     |
| Gly | Leu | Leu | Leu | Gln | Ser | Val | Val | Leu | Gly | Phe | Met | Ser | Leu | Gly | Val |
|     |     |     | 340 |     |     |     |     | 345 |     |     |     |     | 350 |     |     |
| Glu | Phe | Leu | Gly | Lys | Lys | Ile | Gly | Gly | Ala | Lys | Arg | Leu | Trp | Gly | Ile |
|     |     | 355 |     |     |     |     | 360 |     |     |     |     | 365 |     |     |     |
| Leu | Asn | Phe | Val | Leu | Ala | Ile | Cys | Leu | Ala | Met | Thr | Ile | Leu | Val | Thr |
|     | 370 |     |     |     |     | 375 |     |     |     |     | 380 |     |     |     |     |
| Lys | Met | Ala | Glu | Lys | Ser | Arg | Gln | His | Asp | Pro | Ala | Gly | Thr | Leu | Met |
| 385 |     |     |     |     | 390 |     |     |     |     | 395 |     |     |     |     | 400 |
| Gly | Pro | Thr | Pro | Gly | Val | Lys | Ile | Gly | Ala | Leu | Leu | Leu | Phe | Ala | Ala |
|     |     |     |     | 405 |     |     |     |     | 410 |     |     |     |     | 415 |     |
| Leu | Gly | Ile | Pro | Leu | Ala | Ala | Thr | Phe | Ser | Ile | Pro | Phe | Ala | Leu | Ala |
|     |     |     | 420 |     |     |     |     | 425 |     |     |     |     | 430 |     |     |
| Ser | Ile | Phe | Ser | Ser | Asn | Arg | Gly | Ser | Gly | Gln | Gly | Leu | Ser | Leu | Gly |
|     |     | 435 |     |     |     |     | 440 |     |     |     |     | 445 |     |     |     |
| Val | Leu | Asn | Leu | Ala | Ile | Val | Val | Pro | Gln | Met | Leu | Val | Ser | Leu | Val |
|     | 450 |     |     |     |     | 455 |     |     |     |     | 460 |     |     |     |     |
| Gly | Gly | Pro | Trp | Asp | Asp | Leu | Phe | Gly | Gly | Gly | Asn | Leu | Pro | Gly | Phe |
| 465 |     |     |     |     | 470 |     |     |     |     | 475 |     |     |     |     | 480 |
| Val | Val | Gly | Ala | Val | Ala | Ala | Ala | Ala | Ser | Ala | Val | Leu | Ala | Leu | Thr |
|     |     |     |     | 485 |     |     |     |     | 490 |     |     |     |     | 495 |     |
| Met | Leu | Pro | Ser | Pro | Pro | Ala | Asp | Ala | Lys | Pro | Ala | Val | Ala | Met | Gly |
|     |     |     | 500 |     |     |     |     | 505 |     |     |     |     | 510 |     |     |
| Leu | Ser | Ile | Lys |     |     |     |     |     |     |     |     |     |     |     |     |
|     |     | 515 |     |     |     |     |     |     |     |     |     |     |     |     |     |

We claim:

1. An isolated DNA sequence comprising the coding region of an oligosaccharide transporter gene derived from a potato or spinach plant.

2. A DNA sequence according to claim 1, wherein said sequence comprises the following nucleotide sequence (Seq-ID No 1):

```
AAAAACACAC ACCCAAAAAA AAAACACTAC GACTATTTCA AAAAAAACAT TGTTACTAGA          60

AATCTTATT  ATG GCA GGA AGA AAT ATA AAA AAT GGT GAA AAT AAC                105
           Met Ala Gly Arg Asn Ile Lys Asn Gly Glu Asn Asn
           1               5                   10

AAG ATT GCG GGT TCT TCT CTT CAC TTA GAG AAG AAC CCA ACA ACT                150
Lys Ile Ala Gly Ser Ser Leu His Leu Glu Lys Asn Pro Thr Thr
        15              20                  25

CCC CCC GAG GCC GAG GCT ACC TTA AAG AAG CTC GGC CTC GTG GCT                195
Pro Pro Glu Ala Glu Ala Thr Leu Lys Lys Leu Gly Leu Val Ala
        30              35                  40

TCA GTA GCG GCC GGG GTT CAG TTC GGG TGG GCT TTA CAG CTC TCC                240
Ser Val Ala Ala Gly Val Gln Phe Gly Trp Ala Leu Gln Leu Ser
        45              50                  55

CTA CTG ACC CCG TAC GTC CAA CTA CTG GGC ATT CCC CAC ACT TGG                285
Leu L:eu Thr Pro Tyr Val Gln Leu Leu Gly Ile Pro His Thr Trp
        60              65                  70

GCC GCC TAC ATC TGG TTG TGC GGC CCA ATC TCG GGG ATG ATT GTC                330
Ala Ala Tyr Ile Trp Leu Cys Gly Pro Ile Ser Gly Met Ile Val
        75              80                  85

CAG CCA TTG GTC GGG TAC TAT AGT GAC CGG TGC ACC TCC CGC TTC                375
Gln Pro Leu Val Gly Tyr Tyr Ser Asp Arg Cys Thr Ser Arg Phe
        90              95                  100

GGC CGA CGT CGC CCC TTC ATT GCA GCA GGG GCG GCT CTA GTG GCC                420
Gly Arg Arg Arg Pro Phe Ile Ala Ala Gly Ala Ala Leu Val Ala
        105             110                 115

GTA GCG GTG GGG CTA ATC GGA TTC GCC GCC GAT ATC GGC GCA GCG                465
Val Ala Val Gly Leu Ile Gly Phe Ala Ala Asp Ile Gly Ala Ala
        120             125                 130

TCG GGT GAT CCA ACG GGA AAC GTG GCA AAA CCC CGG GCC ATC GCG                510
Ser Gly Asp Pro Thr Gly Asn Val Ala Lys Pro Arg Ala Ile Ala
        135             140                 145

GTG TTT GTG GTC GGG TTT TGG ATC CTC GAC GTG GCT AAC AAC ACC                555
Val Phe Val Val Gly Phe Trp Ile Leu Asp Val Ala Asn Asn Thr
        150             155                 160

CTG CAA GGC CCA TGC AGG GCG TTG TTA GCA GAC ATG GCC GCC GGG                600
Leu Gln Gly Pro Cys Arg Ala Leu Leu Ala Asp Met Ala Ala Gly
        165             170                 175

TCG CAA ACC AAA ACC CGG TAC GCT AAC GCC TTC TTC TCC TTC TTC                645
Ser Gln Thr Lys Thr Arg Tyr Ala Asn Ala Phe Phe Ser Phe Phe
        180             185                 190

ATG GCG TTA GGA AAC ATC GGA GGG TAC GCC GCC GGT TCA TAC AGC                690
Met Ala Leu Gly Asn Ile Gly Gly Tyr Ala Ala Gly Ser Tyr Ser
        195             200                 205

CGC CTC TAC ACG GTG TTC CCC TTT ACC AAA ACC GCC GCC TGC GAC                735
Arg Leu Tyr Thr Val Phe Pro Phe Thr Lys Thr Ala Ala Cys Asp
        210             215                 220

GTC TAC TGC GCC AAT CTA AAA TCC TGC TTC TTC ATC TCC ATC ACA                780
Val Tyr Cys Ala Asn Leu Lys Ser Cys Phe Phe Ile Ser Ile Thr
        225             230                 235

CTC CTA ATC GTC CTC ACA ATC CTA GCA CTT TCC GTC GTA AAA GAG                825
Leu Leu Ile Val Leu Thr Ile Leu Ala Leu Ser Val Val Lys Glu
        240             245                 250

CGT CAA ATC ACA ATC GAC GAA ATC CAA GAA GAA GAA GAC TTA AAA                870
Arg Gln Ile Thr Ile Asp Glu Ile Gln Glu Glu Glu Asp Leu Lys
        255             260                 265

AAC AGA AAC AAT AGC AGC GGT TGT GCA AGA CTA CCG TTC TTC GGA                915
Asn Arg Asn Asn Ser Ser Gly Cys Ala Arg Leu Pro Phe Phe Gly
        270             275                 280
```

| | | |
|---|---|---|
| CAA TTA ATA GGC GCT CTC AAA GAT CTA CCA AAA CCA ATG CTA ATC<br>Gln Leu Ile Gly Ala Leu Lys Asp Leu Pro Lys Pro Met Leu Ile<br>285 290 295 | | 960 |
| CTA TTA CTA GTA ACA GCC CTA AAT TGG ATC GCA TGG TTT CCA TTC<br>Leu Leu Leu Val Thr Ala Leu Asn Trp Ile Ala Trp Phe Pro Phe<br>300 305 310 | | 1005 |
| TTG TTG TTC GAT ACT GAT TGG ATG GGT AAA GAA GTG TAC GGT GGT<br>Leu Leu Phe Asp Thr Asp Trp Met Gly Lys Glu Val Tyr Gly Gly<br>315 320 325 | | 1050 |
| ACA GTC GGA GAA GGT AAA TTG TAC GAC CAA GGA GTT CAT GCC GGT<br>Thr Val Gly Glu Gly Lys Leu Tyr Asp Gln Gly Val His Ala Gly<br>330 335 340 | | 1095 |
| GCC TTA GGT CTG ATG ATT AAC TCC GTT GTC TTA GGT GTT ATG TCG<br>Ala Leu Gly Leu Met Ile Asn Ser Val Val Leu Gly Val Met Ser<br>345 350 355 | | 1140 |
| TTG AGT ATT GAA GGT TTG GCT CGT ATG GTA GGC GGT GCT AAA AGG<br>Leu Ser Ile Glu Gly Leu Ala Arg Met Val Gly Gly Ala Lys Arg<br>360 365 370 | | 1185 |
| TTA TGG GGA ATT GTC AAT ATT ATT CTT GCT GTT TGT TTA GCT ATG<br>Leu Trp Gly Ile Val Asn Ile Ile Leu Ala Val Cys Leu Ala Met<br>375 380 385 | | 1230 |
| ACG GTG TTA GTT ACT AAG TCC GCC GAA CAC TTC CGT GAT AGC CAC<br>Thr Val Leu Val Thr Lys Ser Ala Glu His Phe Arg Asp Ser His<br>390 395 400 | | 1275 |
| CAT ATT ATG GGC TCC GCC GTC CCT CCG CCG CCG CCT GCT GGT GTT<br>His Ile Met Gly Ser Ala Val Pro Pro Pro Pro Pro Ala Gly Val<br>405 410 415 | | 1320 |
| AAG GGT GGC GCT TTG GCT ATC TTT GCC GTT CTT GGT ATC CCT CTT<br>Lys Gly Gly Ala Leu Ala Ile Phe Ala Val Leu Gly Ile Pro Leu<br>420 425 430 | | 1365 |
| GCG ATC ACT TTC AGT ATT CCT TTG GCC TTG GCG TCA ATC TTT TCA<br>Ala Ile Thr Phe Ser Ile Pro Leu Ala Leu Ala Ser Ile Phe Ser<br>435 440 445 | | 1410 |
| GCA TCT TCC GGT TCA GGA CAA GGT CTT TCT CTA GGA GTT CTC AAC<br>Ala Ser Ser Gly Ser Gly Gln Gly Leu Ser Leu Gly Val Leu Asn<br>450 455 460 | | 1455 |
| CTC GCC ATC GTT GTA CCC CAG ATG TTT GTG TCG GTA ACA AGT GGG<br>Leu Ala Ile Val Val Pro Gln Met Phe Val Ser Val Thr Ser Gly<br>465 470 475 | | 1500 |
| CCA TGG GAT GCA ATG TTT GGT GGA GGA AAT TTG CCA GCA TTC GTG<br>Pro Trp Asp Ala Met Phe Gly Gly Gly Asn Leu Pro Ala Phe Val<br>480 485 490 | | 1545 |
| GTG GGA GCT GTA GCA GCA ACA GCC AGT GCA GTT CTT TCA TTT ACA<br>Val Gly Ala Val Ala Ala Thr Ala Ser Ala Val Leu Ser Phe Thr<br>495 500 505 | | 1590 |
| TTG TTG CCT TCT CCA CCC CCT GAA GCT AAA ATT GGT GGG TCC ATG<br>Leu Leu Pro Ser Pro Pro Pro Glu Ala Lys Ile Gly Gly Ser Met<br>510 515 520 | | 1635 |
| GGT GGT CAT TAAGAAATTT AATACTACTC CGTACAATTT AAACCCAAAT<br>Gly Gly His<br>525 | | 1684 |
| TAAAAATGAA AATGAAAATT TTTAACCCAT GTTCGTTACG TTGTAATTAG | | 1734 |
| AGAGAAAAAT GATATATTGA ACGAAGCCGT TAATTTATGC TCCGTTCATC | | 1784 |
| TTGTAATTCT TTTTCTCTCT GCTTTTTTTT TTTTTTTTTA ACGCGACGTG | | 1834 |
| TTTTTGAGAT AAGGAAGGGC TAGATCGAGG ATGGGGGAAT TGGCAAGAAA | | 1884 |
| TTGCTCGGGT ATAAATATTT ATCCCTCTTT GTAATTTTCA GTAACATTTA | | 1934 |

-continued

ATAGCCAGAA ATCAAAAAGT CAAGAAAAAT CGAAA. 1969

3. A DNA sequence according to claim 1, wherein said sequence comprises the following nucleotide sequence (Seq-ID No 3):

```
                                                                    AAAA      4

ATG GAG AAT GGT ACA AAA AGA GAA GGT TTA GGG AAA CTT ACA GTT          49
Met Glu Asn Gly Thr Lys Arg Glu Gly Leu Gly Lys Leu Thr Val
             5                    10                      15

TCA TCT TCT CTA CAA GTT GAA CAG CCT TTA GCA CCA TCA AAG CTA          94
Ser Ser Ser Leu Gln Val Glu Gln Pro Leu Ala Pro Ser Lys Leu
             20                   25                      30

TGG AAA ATT ATA GTT GTA GCT TCC ATA GCT GCT GGT GTT CAA TTT          139
Trp Lys Ile Ile Val Val Ala Ser Ile Ala Ala Gly Val Gln Phe
             35                   40                      45

GGT TGG GCT CTT CAG CTC TCT TTG CTT ACA CCT TAT GTT CAA TTG          184
Gly Trp Ala Leu Gln Leu Ser Leu Leu Thr Pro Tyr Val Gln Leu
             50                   55                      60

CTC GGA ATT CCT CAT AAA TTT GCC TCT TTT ATT TGG CTT TGT GGA          229
Leu Gly Ile Pro His Lys Phe Ala Ser Phe Ile Trp Leu Cys Gly
             65                   70                      75

CCG ATT TCT GGT ATG ATT GTT CAG CCA GTT GTC GGC TAC TAC AGT          274
Pro Ile Ser Gly Met Ile Val Gln Pro Val Val Gly Tyr Tyr Ser
             80                   85                      90

GAT AAT TGC TCC TCC CGT TTC GGT CGC CGC CGG CCA TTC ATT GCC          319
Asp Asn Cys Ser Ser Arg Phe Gly Arg Arg Arg Pro Phe Ile Ala
             95                   100                     105

GCC GGA GCT GCA CTT GTT ATG ATT GCG GTT TTC CTC ATC GGA TTC          364
Ala Gly Ala Ala Leu Val Met Ile Ala Val Phe Leu Ile Gly Phe
             110                  115                     120

GCC GCC GAC CTT GGT CAC GCC TCC GGT GAC ACT CTC GGA AAA GGA          409
Ala Ala Asp Leu Gly His Ala Ser Gly Asp Thr Leu Gly Lys Gly
             125                  130                     135

TTT AAG CCA CGT GCC ATT GCC GTT TTC GTC GTC GGC TTT TGG ATC          454
Phe Lys Pro Arg Ala Ile Ala Val Phe Val Val Gly Phe Trp Ile
             140                  145                     150

CTT GAT GTT GCT AAC AAC ATG TTA CAG GGC CCA TGC AGA GCA CTA          499
Leu Asp Val Ala Asn Asn Met Leu Gln Gly Pro Cys Arg Ala Leu
             155                  160                     165

CTG GCT GAT CTC TCC GGC GGA AAA TCC GGC AGG ATG AGA ACA GCA          544
Leu Ala Asp Leu Ser Gly Gly Lys Ser Gly Arg Met Arg Thr Ala
             170                  175                     180

AAT GCT TTT TTC TCA TTC TTC ATG GCC GTC GGA AAC ATT CTG GGG          589
Asn Ala Phe Phe Ser Phe Phe Met Ala Val Gly Asn Ile Leu Gly
             185                  190                     195

TAC GCC GCC GGT TCA TAT TCT CAC CTC TTT AAA GTA TTC CCC TTC          634
Tyr Ala Ala Gly Ser Tyr Ser His Leu Phe Lys Val Phe Pro Phe
             200                  205                     210

TCA AAA ACC AAA GCC TGC GAC ATG TAC TGC GCA AAT CTG AAG AGT          679
Ser Lys Thr Lys Ala Cys Asp Met Tyr Cys Ala Asn Leu Lys Ser
             215                  220                     225

TGT TTC TTC ATC GCT ATA TTC CTT TTA CTC AGC TTA ACA ACC ATA          724
Cys Phe Phe Ile Ala Ile Phe Leu Leu Leu Ser Leu Thr Thr Ile
             230                  235                     240

GCC TTA ACC TTA GTC CGG GAA AAC GAG CTC CCG GAG AAA GAC GAG          769
Ala Leu Thr Leu Val Arg Glu Asn Glu Leu Pro Glu Lys Asp Glu
             245                  250                     255

CAA GAA ATC GAC GAG AAA TTA GCC GGC GCC GGA AAA TCG AAA GTA          814
Gln Glu Ile Asp Glu Lys Leu Ala Gly Ala Gly Lys Ser Lys Val
             260                  265                     270
```

-continued

| | | | | | | | | | | | | | | | |
|---|---|---|---|---|---|---|---|---|---|---|---|---|---|---|---|
| CCG | TTT | TTC | GGT | GAA | ATT | TTT | GGG | GCT | TTG | AAA | GAA | TTA | CCT | CGA | 859 |
| Pro | Phe | Phe | Gly | Glu 275 | Ile | Phe | Gly | Ala | Leu 280 | Lys | Glu | Leu | Pro | Arg 285 | |
| CCG | ATG | TGG | ATT | CTT | CTA | TTA | GTA | ACC | TGT | TTG | AAC | TGG | ATC | GCG | 904 |
| Pro | Met | Trp | Ile | Leu 290 | Leu | Leu | Val | Thr | Cys 300 | Leu | Asn | Trp | Ile | Ala 305 | |
| TGG | TTT | CCC | TTT | TTC | TTA | TAC | GAT | ACA | GAT | TGG | ATG | GCT | AAG | GAG | 949 |
| Trp | Phe | Pro | Phe | Phe 310 | Leu | Tyr | Asp | Thr | Asp 315 | Trp | Met | Ala | Lys | Glu 320 | |
| GTT | TTC | GGT | GGA | CAA | GTC | GGT | GAT | GCG | AGG | TTG | TAC | GAT | TTG | GGT | 994 |
| Val | Phe | Gly | Gly | Gln 325 | Val | Gly | Asp | Ala | Arg 330 | Leu | Tyr | Asp | Leu | Gly 335 | |
| GTA | CGC | GCT | GGT | GCA | ATG | GGA | TTA | CTG | TTG | CAA | TCT | GTG | GTT | CTA | 1039 |
| Val | Arg | Ala | Gly | Ala 340 | Met | Gly | Leu | Leu | Leu 345 | Gln | Ser | Val | Val | Leu 350 | |
| GGG | TTT | ATG | TCA | CTT | GGG | GTT | GAA | TTC | TTA | GGG | AAG | AAG | ATT | GGT | 1084 |
| Gly | Phe | Met | Ser | Leu 355 | Gly | Val | Glu | Phe | Leu 360 | Gly | Lys | Lys | Ile | Gly 370 | |
| GGT | GCT | AAG | AGG | TTA | TGG | GGA | ATT | TTG | AAC | TTT | GTT | TTG | GCT | ATT | 1129 |
| Gly | Ala | Lys | Arg | Leu 375 | Trp | Gly | Ile | Leu | Asn 380 | Phe | Val | Leu | Ala | Ile 385 | |
| TGC | TTG | GCT | ATG | ACC | ATT | TTG | GTC | ACC | AAA | ATG | GCC | GAG | AAA | TCT | 1174 |
| Cys | Leu | Ala | Met | Thr 390 | Ile | Leu | Val | Thr | Lys 395 | Met | Ala | Glu | Lys | Ser 400 | |
| CGC | CAG | CAC | GAC | CCC | GCC | GGC | ACA | CTT | ATG | GGG | CCG | ACG | CCT | GGT | 1219 |
| Arg | Gln | His | Asp | Pro 405 | Ala | Gly | Thr | Leu | Met 410 | Gly | Pro | Thr | Pro | Gly 415 | |
| GTT | AAA | ATC | GGT | GCC | TTG | CTT | CTC | TTT | GCC | GCC | CTT | GGT | ATT | CCT | 1264 |
| Val | Lys | Ile | Gly | Ala 420 | Leu | Leu | Leu | Phe | Ala 425 | Ala | Leu | Gly | Ile | Pro 430 | |
| CTT | GCG | GCA | ACT | TTT | AGT | ATT | CCA | TTT | GCT | TTG | GCA | TCT | ATA | TTT | 1309 |
| Leu | Ala | Ala | Thr | Phe 435 | Ser | Ile | Pro | Phe | Ala 440 | Leu | Ala | Ser | Ile | Phe 445 | |
| TCT | AGT | AAT | CGT | GGT | TCA | GGA | CAA | GGT | TTG | TCA | CTA | GGA | GTG | CTC | 1354 |
| Ser | Ser | Asn | Arg | Gly 450 | Ser | Gly | Gln | Gly | Leu 455 | Ser | Leu | Gly | Val | Leu 460 | |
| AAT | CTT | GCA | ATT | GTT | GTA | CCA | CAG | ATG | TTG | GTG | TCA | CTA | GTA | GGA | 1399 |
| Asn | Leu | Ala | Ile | Val 465 | Val | Pro | Gln | Met | Leu 470 | Val | Ser | Leu | Val | Gly 475 | |
| GGG | CCA | TGG | GAT | GAT | TTG | TTT | GGA | GGA | GGA | AAC | TTG | CCT | GGA | TTT | 1444 |
| Gly | Pro | Trp | Asp | Asp 480 | Leu | Phe | Gly | Gly | Gly 485 | Asn | Leu | Pro | Gly | Phe | |
| GTA | GTT | GGA | GCA | GTT | GCA | GCT | GCC | GCG | AGC | GCT | GTT | TTA | GCA | CTC | 1489 |
| Val | Val | Gly | Ala | Val 495 | Ala | Ala | Ala | Ala | Ser 500 | Ala | Val | Leu | Ala | Leu 505 | |
| ACA | ATG | TTG | CCA | TCT | CCA | CCT | GCT | GAT | GCT | AAG | CCA | GCA | GTC | GCC | 1534 |
| Thr | Met | Leu | Pro | Ser 510 | Pro | Pro | Ala | Asp | Ala 515 | Lys | Pro | Ala | Val | Ala 520 | |
| ATG | GGG | CTT | TCC | ATT | AAA | TAATTACAAA | AGAAGGAGAA | GAACAACTTT | | | | | | | 1582 |
| Met | Gly | Leu | Ser | Ile 525 | Lys | | | | | | | | | | |

```
TTTTTAATAT TAGTACTTCT CTTTTGTAAA CTTTTTTTAT TTTAGAAAAC        1632

AAACATAACA TGGAGGCTAT CTTTACAAGT GGCATGTCCA TGTATCTTCC        1682

TTTTTTCATA AAGCTCTTTA GTGGAAGAAG AATTAGAGGA AGTTTCCTTT        1732

TAATTTCTTC CAAACAAATG GGGTATGTGT AGTTGTTTTC A.                1773
```

4. A plasmid, comprising a DNA sequence according to claim 1.

5. An isolated DNA sequence, according to claim 1, wherein integration and expression of said sequence into a plant or a plant cell alters the formation and transport of storage materials in said plant or said plant cell relative to a non-transformed plant or plant cell.

6. A method of producing plant cells with oligosaccharide transporter activity, comprising the step of transforming plant cells with a plasmid according to claim 4.

7. A transgenic plant comprising an altered amount of oligosaccharide transporter activity relative to a non-transformed plant, said plant comprising the DNA sequence of claim 1.

8. A plant or plant cell transformed with a plasmid according to claim 4, wherein said plant or plant cell is capable of expressing an altered amount of oligosaccharide transporter activity relative to a non-transformed plant.

9. A method of producing a plant cell with an increased synthesis of sucrose transporter relative to a non-transformed plant, comprising the steps of:

producing a DNA molecule comprising the following sequences:
  i) a promoter which is active in said plant or plant cell,
  ii) a structural DNA sequence, according to claim 1, which allows the transcription of an RNA which in said transgenic plant codes for an oligosaccharide transporter; and transferring and incorporating said DNA molecule into the genome of a plant cell.

10. A recombinant expression vector comprising a DNA sequence encoding an oligosaccharide transporter derived from a potato or spinach plant and a promoter sequence, wherein the promoter is capable of expressing the oligosaccharide transporter gene in a transformed plant cell or transgenic plant.

11. A method of over-expressing an oligosaccharide transporter gene, comprising the step of transforming a plant or a plant cell with plasmid pBin-AR-S21 prepared from plasmid pSK-S21.

12. A method of altering the characteristics of agriculturally useful plants, comprising the step of transforming an agriculturally useful plant with a DNA sequence according to claim 1.

13. A plasmid comprising a coding portion of the DNA sequence according to claim 2.

14. A plasmid comprising a coding portion of the DNA sequence according to claim 3.

15. A method of altering the characteristics of an agriculturally useful plant, comprising the step of transforming an agriculturally useful plant with a DNA sequence according to claim 2.

16. A method of altering the characteristics of an agriculturally useful plant, comprising the step of transforming an agriculturally useful plant with a DNA sequence according to claim 3.

* * * * *